United States Patent
Abi Fadel et al.

(10) Patent No.: US 7,300,754 B2
(45) Date of Patent: Nov. 27, 2007

(54) METHODS FOR DETECTING THE PRESENCE OF OR PREDISPOSITION TO AUTOSOMAL DOMINANT HYPERCHOLESTEROLEMIA

(75) Inventors: Marianne Abi Fadel, Broummana (LB); Catherine Boileau, Paris (FR); Jean-Pierre Rabes, Sevres (FR); Nabil G. Seidah, Québec (CA); Mathilde Varret, Chatillon (FR)

(73) Assignee: Institut National de la Sante et de la Recherche Medicale, Paris Cedex (FR)

( * ) Notice: Subject to any disclaimer, the term of this patent is extended or adjusted under 35 U.S.C. 154(b) by 320 days.

(21) Appl. No.: 10/830,454

(22) Filed: Apr. 23, 2004

(65) Prior Publication Data

US 2004/0248177 A1    Dec. 9, 2004

Related U.S. Application Data

(60) Provisional application No. 60/538,231, filed on Jan. 23, 2004.

(30) Foreign Application Priority Data

Apr. 25, 2003  (EP) ................... 03291025

(51) Int. Cl.
- C12Q 1/68       (2006.01)
- C12P 19/34      (2006.01)
- C07H 21/02      (2006.01)
- C07H 21/04      (2006.01)

(52) U.S. Cl. .................. 435/6; 435/91.2; 536/23.5; 536/24.31

(58) Field of Classification Search .............. None
See application file for complete search history.

(56) References Cited

FOREIGN PATENT DOCUMENTS

WO     WO 01/57081     8/2001

OTHER PUBLICATIONS

NCBI SNP Database, National Center for Biotechnology Information, National Library of Medicine, NIH (Bethesda, MD, USA). SNP printout for the PCSK9 gene.*

Shioji et al. Journal of Human Genetics. 2004. 49:109-114.*

Shibata et al. Psychiatric Genetics. 2005. 15:239.*

Kotowski et al. American Journal of Human Genetics. Mar. 2006. 78: 410-422.*

Seidah et al, The secretory proprotein convertase neural apoptosis-regulated convertase 1 (NARC-1): Liver regeneration and neuronal differentiation, PNAS, Feb. 4, 2003, vol. 100, No. 3, pp. 928-933.

Abifadel et al, Mutations in PCSK9 cause autosomal dominant hypercholesterolemia, Nature Genetics, Jun. 2003, vol. 34, No. 2, pp. 154-156.

Varret et al, A Third Major Locus for Autosomal Dominant Hypercholesterolemia Maps to 1p34.1-p32, Am. J. Hum. Genet., 1999, 64:1378-1387.

Varret et al, Software and database for the analysis of mutations in the human LDL receptor gene, Nucleic Acids Research, 1997, vol. 25, No.1, pp 172-180.

* cited by examiner

Primary Examiner—Carla Myers
(74) Attorney, Agent, or Firm—Nixon & Vanderhye P.C.

(57) ABSTRACT

The present invention discloses the identification of a human hypercholesterolemia causal gene, which can be used for the diagnosis, prevention and treatment of hypercholesterolemia, more particularly familial hypercholesterolemia, as well as for the screening of therapeutically active drugs. The invention more specifically disclosed that mutations in the PCSK9 gene encoding NARC-1 causes autosomal dominant hypercholesterolemia and represent novel targets for therapeutic intervention. The invention can be used in the diagnosis of predisposition to, detection, prevention and/or treatment of coronary heart disease and, cholesterol, lipid and lipoprotein metabolism disorders, including familial hypercholesterolemia, atherogenic dyslipidemia, atherosclerosis, cardiovascular diseases.

5 Claims, 4 Drawing Sheets

Figure 3A:
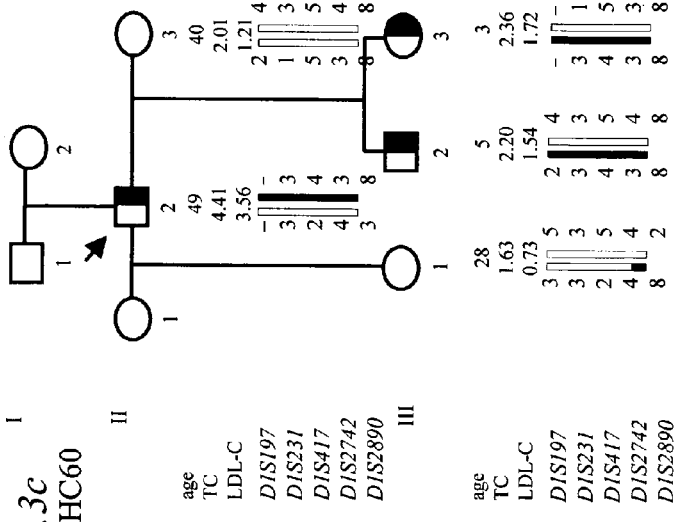

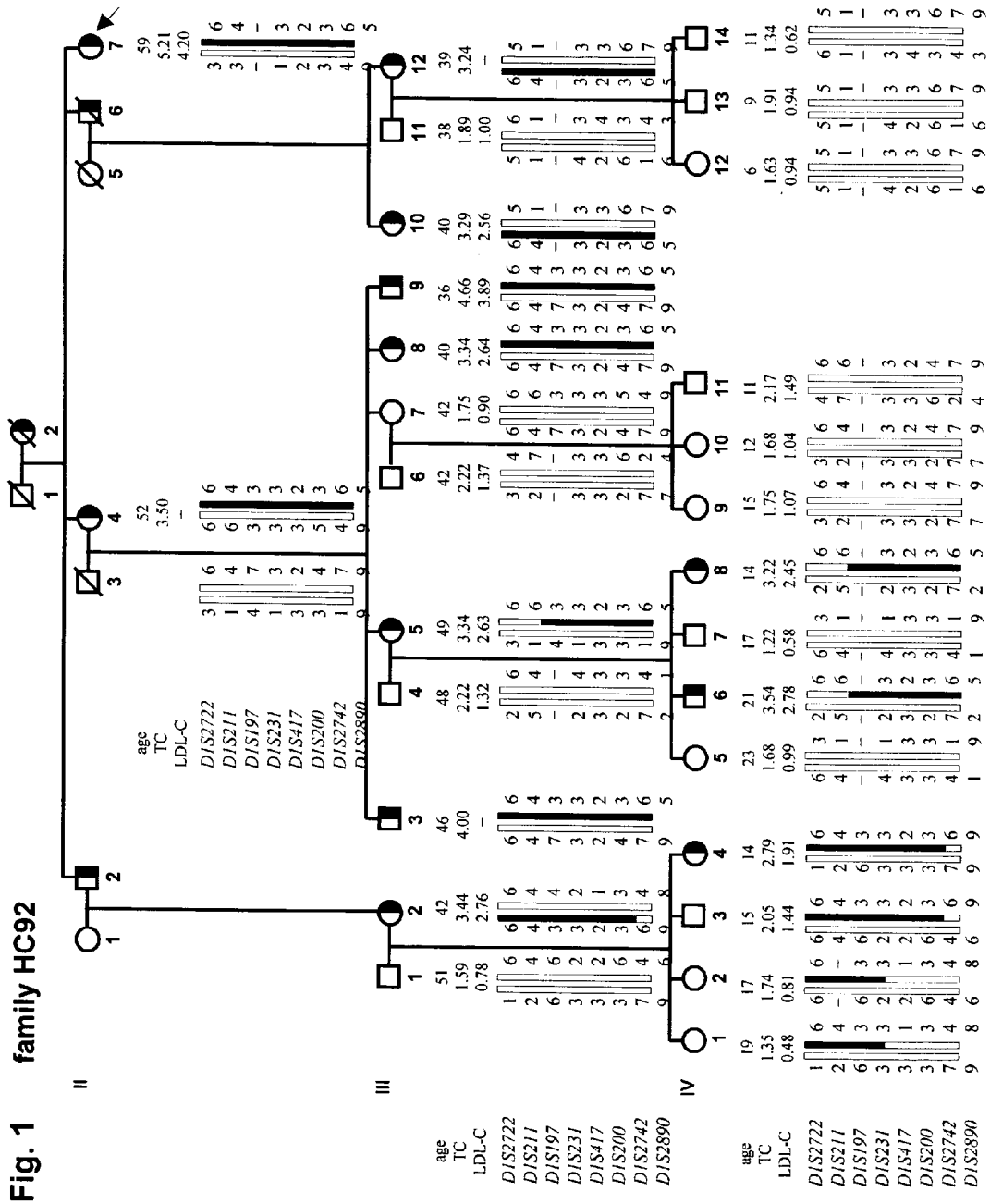
Fig. 1  family HC92

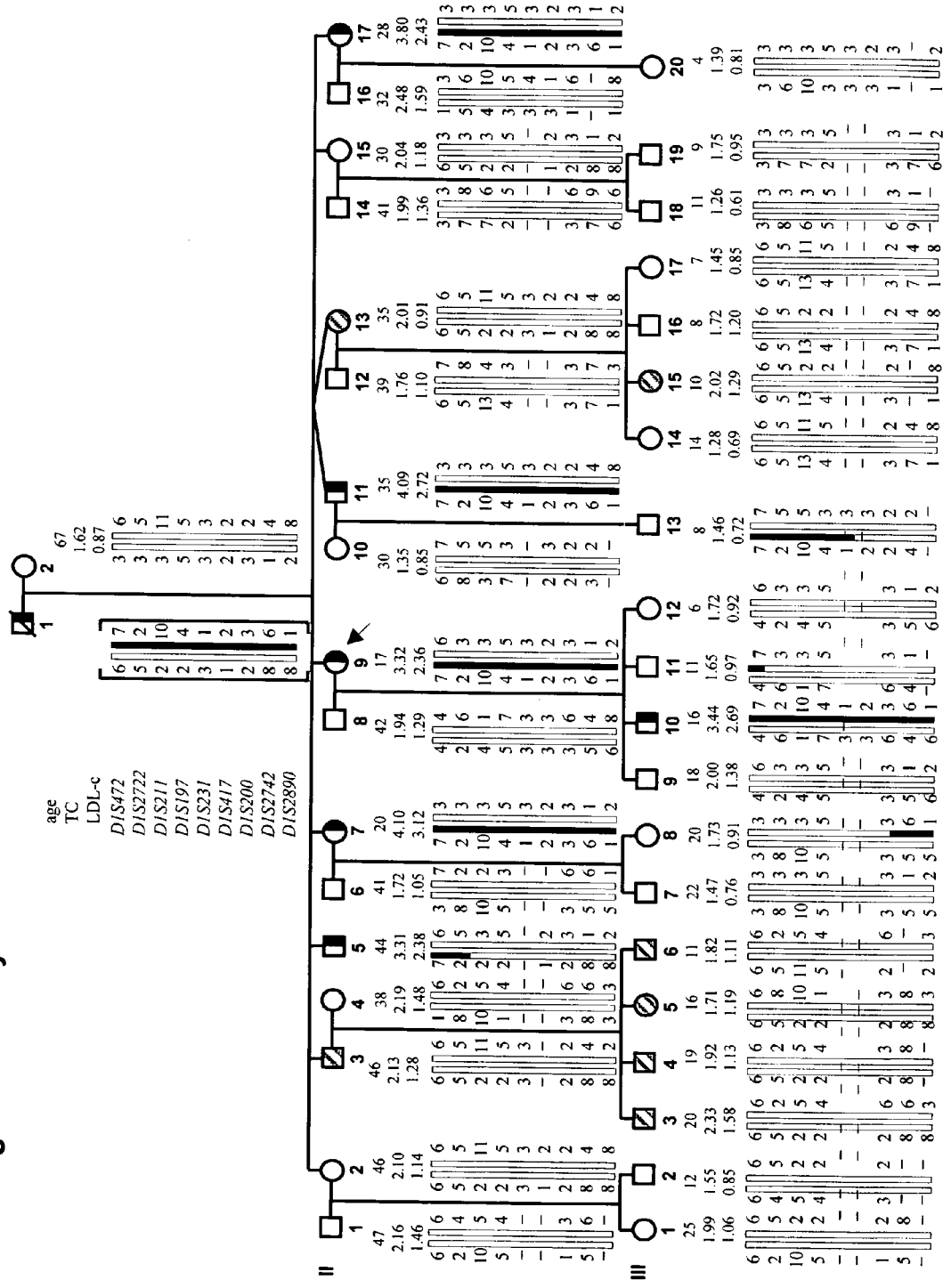
Fig. 2  family HC2

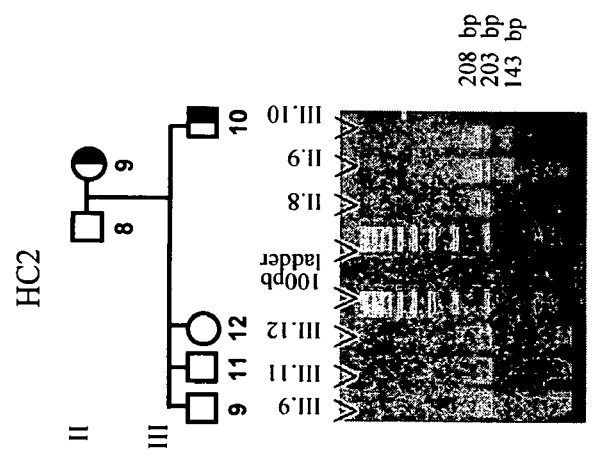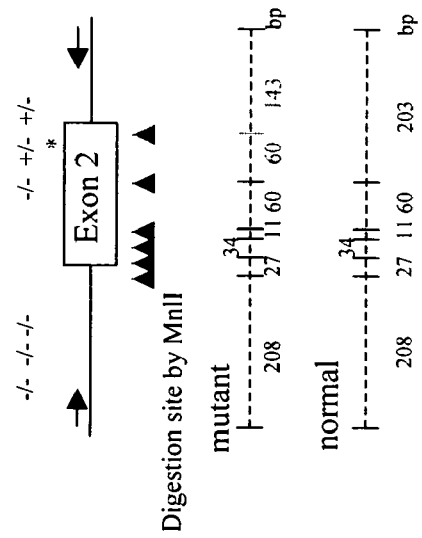

METHODS FOR DETECTING THE PRESENCE OF OR PREDISPOSITION TO AUTOSOMAL DOMINANT HYPERCHOLESTEROLEMIA

This application claims priority to EP Application No. 03 291025.9 filed 25 Apr. 2003 and U.S. Provisional Application No. 60/538,231 filed 23 Jan. 2004. The entire contents of these applications are incorporated herein by reference.

INTRODUCTION

The present invention relates generally to the fields of genetics and medicine. The present invention more particularly discloses the identification of a human hypercholesterolemia causal gene, which can be used for the diagnosis, prevention and treatment of hypercholesterolemia, and more particularly familial hypercholesterolemia ADH, as well as for the screening of therapeutically active drugs. The invention more specifically discloses that mutations in the PCSK9 gene encoding NARC-1 cause autosomal dominant hypercholesterolemia (ADH) and represent novel targets for therapeutic intervention. The invention can be used in the diagnosis of predisposition to, detection, prevention and/or treatment of cholesterol and lipoprotein metabolism disorders, including familial hypercholesterolemia, atherogenic dyslipidemia, atherosclerosis, and more generally cardiovascular diseases (CVD).

BACKGROUND

Atherosclerosis is a disease of the arteries responsible for coronary heart disease (CVD) that underlies most deaths in industrialized countries (Lusis, 2000). Several risk factors for CHD have now been well established: dyslipidemias, hypertension, diabetes, smoking, poor diet, inactivity and stress. The most clinically relevant and common dyslipidemias are characterized by an increase in beta-lipoproteins (VLDL and LDL particles) with hypercholesterolemia in the absence or presence of hypertriglyceridemia (Fredrickson et al, 1967). An isolated elevation of LDL cholesterol is one of the most common risk factors for CVD. Twin studies (Austin et al, 1987) and family data (Perusse, 1989; Rice et al, 1991) have shown the importance of genetic factors in the development of the disease, particularly when its complications occur early in life. Mendelian forms of hypercholesterolemia have been identified: at first the autosomal dominant form (ADH) (Khachadurian, 1964) and later the autosomal recessive form (ARH), initially described as "pseudohomozygous type II hyperlipoproteinemia" (Morganroth et al, 1967).

ADH is an heterogeneous genetic disorder. Its most frequent and archetypal form is Familial Hypercholesterolemia (FH) with a frequency of 1 in 500 for heterozygotes and 1 per million for homozygotes (Goldstein et al, 1973). The disease is co-dominant with homozygotes being affected earlier and more severely than heterozygotes. FH is caused by mutations in the gene that encodes the LDL receptor (Goldstein & Brown, 1978) (LDLR at 19p13.1-p13.3) (MIM 143890). It is characterized by a selective increase of LDL cholesterol levels in plasma giving rise to tendon and skin xanthomas, arcus corneae and cardiovascular deposits leading to progressive and premature atherosclerosis, CHD and mortality (occurring before 55 years). The second form of ADH is Familial Defective apo B-100 (FDB) caused by mutations in the apolipoprotein B gene (APOB at 2p23-p24), encoding the ligand of the LDL receptor (Inneraty et al, 1987) (MIM 144010). The existence of a greater level of genetic heterogeneity in ADH (Saint-Jore et al, 2000) has been reported and the implication of a third locus named HCHOLA3 (formerly FH3) has been detected and mapped at 1p34.1-p32 in a French family (Varret et al, 1999) (MIM 603776). These results were confirmed by Hunt et al. in a large Utah kindred (Hunt et al, 2000).

There is a strong need of identifying genes involved in hypercholesterolemia, more particularly in ADH, in order to understand the mechanisms leading to these disorders and to develop improved diagnosis and therapeutic treatment.

SUMMARY OF THE INVENTION

The inventors have shown that mutations in the PCSK9 gene encoding NARC-1 cause autosomal dominant hypercholesterolemia. They have demonstrated that the NARC-1 protein contributes to cholesterol homeostasis. The invention thus discloses novel targets for diagnosis and therapeutic intervention for hypercholesterolemia, more particularly ADH, CVD, lipid and lipoprotein metabolism disorders, atherogenic dyslipidemia, atherosclerosis, and cardiovascular diseases.

In a first aspect, the invention concerns a PCSK9 gene or a fragment thereof comprising an alteration, said alteration reducing, modifying or abolishing the activity of NARC-1. Preferably, said alteration is a nucleotide substitution. More preferably, said nucleotide substitution leads to an amino acid change in NARC-1 protein. Preferably, said amino acid change is located at or near the catalytic site or a zymogen processing of the NARC-1 protein and decreases the catalytic activity or autocatalytic cleavage of said protein or functional domain, respectively. Alternatively, the alteration affects the splicing of NARC-1 mRNA.

The invention also concerns a corresponding NARC-1 protein or a fragment thereof comprising an alteration, said alteration reducing, modifying or abolishing the activity of NARC-1. Preferably, the alteration is located at the catalytic site of the NARC-1 protein and decreases its catalytic activity or at a zymogen processing site of NARC-1 and decreases its autocatalytic cleavage. In an other preferred embodiment, the alteration is located near the catalytic site of the NARC-1 protein and decreases its catalytic activity or near the zymogen processing sites of NARC-1 and decreases its autocatalytic cleavage.

An aspect of the present invention concerns a method of genotyping in a subject a polymorphism of the PCSK9 gene, preferably a polymorphism disclosed in Table 2. The invention also concerns a method of associating one or several polymorphism(s) of the PCSK9 gene, preferably one or several polymorphism(s) disclosed in Table 2 to a disease or a disorder.

An other aspect of this invention relates to a method of detecting the presence of or predisposition to hypercholesterolemia, more particularly ADH, or lipid and lipoprotein metabolism disorders in a subject, the method comprising detecting in a sample from the subject the presence of an alteration in the PCSK9 gene or in the NARC-1 protein, the presence of said alteration being indicative of the presence or predisposition to hypercholesterolemia, more particularly ADH, or lipid and lipoprotein metabolism disorders. In a most preferred embodiment, said alteration reduces, modifies, or abolishes the activity of NARC-1. Optionally, the method further comprises detecting the presence of an alteration in the LDL receptor and/or the apolipoprotein B in said sample.

The invention also relates to a diagnostic kit comprising primers, probes and/or antibodies for detecting in a sample from a subject the presence of an alteration in the PCSK9 gene or in the NARC-1 protein, in the NARC-1 RNA or polypeptide expression, and/or in NARC-1 activity. Optionally, said diagnostic kit further comprises reagents for detecting in a sample from a subject the presence of an alteration in the LDL receptor and/or the apolipoprotein B.

A further aspect of the invention relates to the use of a functional NARC-1, preferably a wild-type NARC-1 protein or a nucleic acid encoding the same, in the manufacture of a pharmaceutical composition for treating or preventing hypercholesterolemia, more particularly ADH, and/or lipid and lipoprotein metabolism disorders in a subject. The invention also relates to the use of a biologically active compound which modulates NARC-1 activity, in the manufacture of a pharmaceutical composition for treating or preventing hypercholesterolemia, more particularly ADH, and/or lipid and lipoprotein metabolism disorders in a subject. The invention also relates to a method for treating or preventing hypercholesterolemia, more particularly ADH, and/or lipid and lipoprotein metabolism disorders in a subject comprising administering to said subject a functional NARC-1, preferably a wild-type NARC-1 protein or a nucleic acid encoding the same. The invention further relates to a method for treating or preventing hypercholesterolemia, more particularly ADH, and/or lipid and lipoprotein metabolism disorders in a subject comprising administering to said subject a biologically active compound which modulates NARC-1 activity.

An additional aspect of this invention relates to methods of selecting biologically active compounds that modulate the activity of NARC-1 protein, typically of an altered NARC-1 polypeptide. The compounds are more particularly suitable for treating hypercholesterolemia, more particularly ADH, and/or lipid and lipoprotein metabolism disorders.

LEGEND TO FIGURES

FIG. 1: Family HC92 pedigree and genetic analysis with markers spanning the 1p34.1-p32 region Affected subjects present with a history of tendon xanthomas (HC92-II-7 and III-3), CHD, early myocardial infarction (HC92-II-2 and II-6) and stroke (HC92-II-4). The affected allele is represented by the filled bars. Age (in years) at lipid measurement, total and LDL cholesterol (in g/L; untreated values for affected members) are given.

FIG. 2: Genetic analysis of family HC2

Pedigree of the HC2 family is shown. Half-blackened symbols indicate affected members, unblackened symbols indicate unaffected members, and hatched symbols indicate members with an unknown phenotypic status. The haplotype in brackets of subject HC2-I-1 was unequivocally deduced. Selected markers spanning the 1p34.1-p32 region are displayed to the left of the pedigrees. The affected allele is represented by the filled bars. Age (in years) at lipid measurement, total and LDL cholesterol (in g/L; untreated values for affected members) are given.

FIG. 3: Genetic analysis and mutation detection in families HC92 and HC60 a, Results of LINKMAP analyses in the HC92 family indicating a maximum lod score for D1S2742 at θ=0. PCSK9 maps 1.2 Mb to this marker. b, Mutation in family HC92. The proband (HC92-II-7) is heterozygous for a T→A substitution in exon 2 at nucleotide 625 (S127R). c, Family pedigree and genetic analysis of family HC60. d, Sequence analysis in family HC60. The proband (HC60-II-2) is heterozygous for a T→C substitution in exon 4 at nucleotide 890 predicting a substitution at 216 of leucine for the conserved phenylalanine (F216L).

FIG. 4: Mutations study a, Segregation of the S127R mutation in part of family HC2. The T→A substitution at nucleotide 625 creates a new recognition cleavage site for restriction digestion by MnlI (represented by *). After electrophoretic migration on a 2% agarose gel, fragments of 208, 203 and 60 bp were distinguished in the normal allele, while fragments of 208, 143 and 60 bp appeared in the mutated alleles (the 203 bp normal fragment was divided in fragments of 143 and 60 bp and the two 60 bp fragments generated comigrated). The proband (HC2-II-9) and one of her children (HC2-III-10) were observed to be heterozygous for the S127R mutation (as indicated by both the 203 and 143 bp bands).

b, The amino acid sequence alignment for NARC-1 shows conservation of the serine at codon 127 between human, mouse and rat. DNA sequences of the normal and mutant genes are shown above and below the amino acid sequences, respectively.

c, The amino acid sequence alignment for NARC-1 shows conservation of the phenylalanine at codon 216 between human, mouse and rat. DNA sequences of the normal and mutant genes are shown above and below the amino acid sequences, respectively.

DETAILED DESCRIPTION OF THE INVENTION

Definition

The PCSK9 gene (or NARC-1 gene) encodes the NARC-1 protein or polypeptide. The NARC-1 protein is translated as a pre-protein which is autocatalytically processed into a mature NARC-1 protein. The sequence of the NARC-1 gene has been described in patent applications WO 01/57081 and WO 02/14358, and partly characterized in Seidah et al (2003). The residues of the NARC-1 catalytic site consist in Asp-186, Ser-188, His-226, Asn-317 and Ser-386. NARC-1 presents two zymogen processing sites: a first one comprising residues 78 to 82 and having a primary cleavage site located at position 82; a second one comprising residues 138 to 142 and having a putative secondary cleavage site located at position 142. The biological function of NARC-1 and the implication of this protein in hypercholesterolemia and lipid and lipoprotein metabolism disorders were unknown.

Within the context of this invention, the PCSK9 gene locus designates all PCSK9 sequences or products in a cell or organism, including PCSK9 coding sequences, PCSK9 non-coding sequences (e.g., introns, 5' and 3' UTR), PCSK9 regulatory sequences controlling transcription and/or translation (e.g., promoter, enhancer, terminator, etc.), as well as all corresponding expression products, such as PCSK9 RNAs (e.g. mRNA) and NARC-1 polypeptides (e.g., a pre-protein and a mature protein).

The term "gene" shall be construed to include any type of coding nucleic acid, including genomic DNA, complementary DNA (cDNA), synthetic or semi-synthetic DNA, as well as any form of corresponding RNA. The term gene particularly includes recombinant nucleic acids encoding NARC-1, i.e., any non naturally occurring nucleic acid molecule created artificially, e.g., by assembling, cutting, ligating or amplifying sequences. A PCSK9 gene is typically double-stranded, although other forms may be contemplated, such as single-stranded. PCSK9 genes may be obtained from various sources and according to various techniques known in the art, such as by screening DNA libraries or by amplification from various natural sources. Recombinant nucleic acids may be prepared by conventional techniques, including chemical synthesis, genetic engineering, enzymatic techniques, or a combination thereof. A particular example of a PCSK9 gene comprises SEQ ID NO: 1.

The indicated positions in a PCSK9 gene and a NARC-1 protein refer to the positions in the sequences of SEQ ID No 1 and SEQ ID No 2, respectively.

The term "hybridize under stringent conditions" means that two nucleic acid fragments are capable of hybridization to one another under standard hybridization conditions described in Sambrook et al., Molecular Cloning: A Laboratory Manual (1989) Cold Spring Harbor Laboratory Press, New York, USA. More specifically, "stringent conditions" as used herein refer to hybridization at 65° C. in a hybridization buffer consisting of 250 mmol/l sodium phosphate buffer pH 7.2, 7% (w/v) SDS, 1% (w/v) BSA, 1 mmol/l EDTA and 0.1 mg/ml single-stranded salmon sperm DNA.

Gene & Protein

The invention concerns an isolated or recombinant PCSK9 gene comprising an alteration causing hypercholesterolemia, more particularly ADH, and/or lipid and lipoprotein metabolism disorders.

The altered PCSK9 gene comprises an alteration leading to a decrease or a complete loss of NARC-1 activity, or to a new NARC-1 activity. This decrease, loss, or new activity can be due to the decrease or loss of the activity of NARC-1 enzyme, to the decrease of NARC-1 stability (either at the stage of nucleic acid or proprotein or protein), to a change of substrate specificity of NARC-1 or to the disturbance or impediment of the NARC-1 polymerization. This decrease or loss of NARC-1 activity can be due to a NARC-1 alteration leading to a decrease or loss of the pro-NARC-1 maturation, either at the first cleavage or the second one or both. The alteration can also affect the catalytic activity by modifying the catalytic site of NARC-1 or its substrate recognition site. Furthermore, the alteration can affect the splicing of the NARC-1 mRNA, leading to an alternative splicing product.

The invention concerns an isolated or recombinant PCSK9 gene or fragment thereof comprising an alteration, wherein said alteration reduces, modifies or abolishes the activity of NARC-1. Preferably, said alteration is a nucleotide substitution. More preferably, said nucleotide substitution leads to an amino, acid change in NARC-1 protein. Preferably, said amino acid change is located at (e.g., within) the catalytic site of the NARC-1 protein and decreases its catalytic activity, or is located at a zymogen processing site of NARC-1 and decreases its autocatalytic cleavage. In an other preferred embodiment, said amino acid change is located near the catalytic site of the NARC-1 protein and decreases its catalytic activity or near the zymogen processing sites of NARC-1 and decreases its autocatalytic cleavage. Alternatively, the alteration may affect the splicing of NARC-1 mRNA. More specifically, said alteration can be is a substitution at nucleotide 625 and/or 890 of SEQ ID No 1. More preferably, said alteration is selected from the group consisting of a T→A substitution at nucleotide 625 of SEQ ID No 1, a T→C substitution at nucleotide 890 of SEQ ID No 1 and a combination thereof. In a further embodiment, said alteration is selected from the group consisting of a substitution at nucleotides 476-478 of SEQ ID No 1, a substitution at nucleotides 482-484 of SEQ ID No 1, a substitution at nucleotides 488-490 of SEQ ID No 1, a substitution at nucleotides 485-490 of SEQ ID No 1, a substitution at nucleotides 548-553 of SEQ ID No 1, a substitution at nucleotides 479-481, 491-493 and 578-580 of SEQ ID No 1, a substitution at nucleotides 620-622 of SEQ ID No 1, a substitution at nucleotides 656-658 of SEQ ID No 1, a substitution at nucleotides 671-673 of SEQ ID No 1, a substitution at nucleotides 920-922 of SEQ ID No 1, and a substitution at nucleotides 1193-1195 of SEQ ID No 1.

The invention also concerns an isolated or recombinant PCSK9 gene or fragment thereof comprising at least one alteration, wherein said alteration is selected from the group consisting of the polymorphisms listed in Table 2 and in Table 4.

The invention relates to an isolated or purified NARC-1 protein or a fragment thereof comprising an alteration, wherein said alteration reduces, modifies or abolishes the activity of NARC-1. Preferably, the alteration is located at the catalytic site of the NARC-1 protein and decreases its catalytic activity or at a zymogen processing site of NARC-1 and decreases its autocatalytic cleavage. In an other preferred embodiment, the alteration is located near the catalytic site of the NARC-1 protein and decreases its catalytic activity or near the zymogen processing sites of NARC-1 and decreases its autocatalytic cleavage. More preferably, said alteration can be selected from the group consisting of a substitution of the residue Serine at position 127, a substitution of the residue Phenylalanine at position 216 and a combination thereof. Still more preferably, said alteration is selected from the group consisting of a substitution of the residue Serine at position 127 of SEQ ID No 2 by an Arginine (S127R), a substitution of the residue Phenylalanine at position 216 of SEQ ID No 2 by a Leucine (F216L) and a combination thereof. In a further embodiment, said alteration is selected from the group consisting of a substitution of the residue Tyrosine at position 78 of SEQ ID No 2, a substitution of the residue Valine at position 80 of SEQ ID No 2, a substitution of the residue Leucine at position 82 of SEQ ID No 2, a substitution of the residues Valine at positions 79, 80 and 81 of SEQ ID No 2, a substitution of the residues Alanines at positions 102 and 103 of SEQ ID No 2, a substitution of the residues Valine at position 79, Lysine at position 83, and Leucine at position 112 of SEQ ID No 2, a substitution of the residue Methionine at position 126 of SEQ ID No 2, a substitution of the residue Proline at position 138 of SEQ ID No 2, a substitution of the residue Isoleucine at position 143 of SEQ ID No 2, a substitution of the residue Histidine at position 226 of SEQ ID No 2, and a substitution of the residue Asparagine at position 317 of SEQ ID No 2. Preferably, said alteration is selected from the group consisting of a substitution of the residue Tyrosine at position 78 of SEQ ID No 2 by an Alanine (Y78A), a substitution of the residue Valine at position 80 of SEQ ID No 2 by an Alanine or a Leucine (V80A or V80L), a substitution of the residue Leucine at position 82 of SEQ ID No 2 by an Alanine, a Valine or a Proline (L82A, L82V or L82P), a substitution of the residues Valine at positions 79, 80 and 81 of SEQ ID No 2 by an Arginine, an Arginine and a Leucine, respectively (V79R, V80R and V81L), a substitution of the residues Alanines at positions 102 and 103 of SEQ ID No 2 by Arginines (A102R and A103R), a substitution of the residues Valine at position 79, Lysine at position 83, and Leucine at position 112 of SEQ ID No 2 by an Isoleucine, a Methionine, a Proline, respectively (V79I, K83M and L112P), a substitution of the residue Methionine at position 126 of SEQ ID No 2 by an Alanine (M126A), a substitution of the residue Proline at position 138 of SEQ ID No 2 by a Tyrosine (P138Y), a substitution of the residue Isoleucine at position 143 of SEQ ID No 2 by a Proline (I143P), a substitution of the residue Histidine at position 226 of SEQ ID No 2 by an Alanine (H226A), and a substitution of the residue Asparagine at position 317 of SEQ ID No 2 by an Alanine (N317A). Alternatively, said alteration can be selected from the group consisting of a substitution of the residue Arginine at position 218 of SEQ ID No 2, a substitution of the residue Arginine at position 237 of SEQ ID No 2 and a combination thereof, more preferably a substitution of the residue Arginine at position 218 of SEQ ID No 2 by a Serine (R218S) or a substitution of the residue Arginine at position 237 of SEQ ID No 2 by a Tryptophane (R237W) or a combination thereof.

The invention also relates to an isolated or purified NARC-1 protein or a fragment thereof comprising an alteration, wherein said alteration is selected from the group consisting of an insertion of a residue Leucine at position 15 of SEQ ID No 2, a substitution of the residue Arginine at position 46 of SEQ ID No 2 by a Leucine (R46L), a substitution of the residue Alanine at position 53 of SEQ ID No 2 by a Valine (A53V), a substitution of the residue Isoleucine at position 474 of SEQ ID No 2 by a Valine (I474V), a substitution of the residue Glutamic acid at position 670 of SEQ ID No 2 by a Glycine (E670G) and a combination thereof. The invention also relates to an isolated or purified NARC-1 protein or a fragment thereof comprising an alteration disclosed in Table 4.

The invention further relates to a recombinant nucleic acid encoding a NARC-1 protein or a fragment thereof comprising an alteration according to the present invention, a vector comprising said nucleic acid, a host cell comprising said vector or said recombinant nucleic acid, and a non-human host organism comprising said recombinant nucleic acid, said vector or said host cell.

Therefore, the invention concerns an isolated or recombinant PCSK9 gene and/or NARC-1 protein comprising an alteration causing hypercholesterolemia, more particularly ADH, said alteration reducing, modifying or abolishing the activity of NARC-1. In this context, by modifying is intended a change of specificity of the NARC-1 protein. Optionally, said alteration decreases or abolishes the stability of the NARC-1 protein. Optionally, said alteration decreases or abolishes the stability of mRNA encoding NARC-1. Optionally, said alteration reduces the transcription rate of the PCSK9 gene. Optionally, said alteration decreases or abolishes the activity of the NARC-1 protein. Optionally, said alteration decreases or abolishes the specificity of NARC-1 for at least one of its natural substrates. Optionally, said alteration introduces a new specificity of NARC-1 for an unusual substrate. Said unusual substrate is preferably involved in cholesterol and/or lipoprotein metabolism. Optionally, said alteration hinders or prevents the NARC-1 polymerization. Optionally, said alteration affects the catalytic site of NARC-1. Optionally, said alteration affects substrate recognition site of NARC-1. Optionally, said alteration affects the processing of pro-NARC-1 in NARC-1. More particularly, said alteration reduces or prevents the autocatalytic cleavage at one of the two zymogen processing sites or at both zymogen processing sites. Optionally, said alteration modifies the association between the NARC-1 and its prosegment, for example by increasing or decreasing their interaction.

By "decrease", it is intended within the context of this invention that the assessed parameter is between 10% and 90% of the parameter value with a wild-type NARC-1 protein in a wild-type environment. More preferably, said assessed parameter is between 25% and 75% of the parameter value with a wild-type NARC-1 protein in a wild-type environment. By "abolish", it is intended within the context of this invention that the assessed parameter is less than 10% of the parameter value with a wild-type NARC-1 protein in a wild-type environment. More preferably, said assessed parameter is less than 5% of the parameter value with a wild-type NARC-1 protein in a wild-type environment. Still more preferably, said assessed parameter is less than 1% of the parameter value with a wild-type NARC-1 protein in a wild-type environment.

In a particular embodiment, said alteration decreases or abolishes the catalytic activity of NARC-1. Preferably, said alteration is located near the catalytic site of the NARC-1 protein. Preferably, this alteration is located near a residue of the catalytic site selected from the group consisting of Aspartic acid at position 186, Serine at position 188, Histidine at position 226, Asparagine at position 317 and Serine at position 386. More preferably, this alteration is located near the histidine in position 226. Alternatively, said alteration can be located at one or several residues of the catalytic site selected from the group consisting of Aspartic acid at position 186, Serine at position 188, Histidine at position 226, Asparagine at position 317 and Serine at position 386.

In an other preferred embodiment, said alteration decreases the autocatalytically cleavage of the NARC-1 protein. Preferably, said alteration is located near the zymogen processing sites of NARC-1. Said zymogen processing sites are located at positions 78-82 and 138-142. Alternatively, said alteration can be located at one or several residues of the zymogen processing sites of NARC-1.

In terms of amino acid sequence, the term "near" designates, within the context of this invention, an alteration located at less than 90 amino acids, preferably 60-30 amino acids, more preferably 20 amino acids, from one residue of the catalytic site or the zymogen processing site. It is also intended that the term "near" does not include residues that form part of the catalytic site or of the zymogen processing site, as defined in the present invention.

In terms of nucleotide sequence, the term "near" indicates that the alteration is located at less than 270 nucleotides, preferably 180-90 nucleotides, more preferably 60 nucleotides, from one nucleotide comprised in a codon encoding a residue of the catalytic site or of the zymogen processing site. Such alteration preferably changes the codon, thereby changing the amino acid at that position in the protein sequence.

In a particular embodiment, the invention concerns an isolated or recombinant PCSK9 gene and/or an isolated or purified NARC-1 protein comprising an alteration, said alteration being preferably located at the following positions: 1-30, 32-66, 68-77, 83-225, 227-532 and 534-692 of SEQ ID No 2.

Said alteration of the PCSK9 gene can be a mutation (e.g., a nucleotide substitution), a deletion or an addition of at least one nucleotide. Preferably, said alteration is a point mutation. More preferably, said mutation is selected from the group consisting of a substitution of the nucleotide at position 625 and/or 890. More preferably, said mutation is selected from the group consisting of a T→A substitution at nucleotide 625 of SEQ ID No 1, a T→C substitution at nucleotide 890 of SEQ ID No 1 and a combination thereof. In this regard, a specific object of the invention concerns a polynucleotide sequence of SEQ ID No 1 or a polynucleotide comprising a fragment of SEQ ID No 1, said polynucleotide comprising either the nucleotide A at position 625 or the nucleotide C at position 890 or a combination thereof. An other specific object of the present invention concerns a polynucleotide sequence of SEQ ID No 3 or a polynucleotide comprising a fragment of SEQ ID No 3, said polynucleotide comprising either the nucleotide A at position 5158 or the nucleotide C at position 13539 or a combination thereof.

A fragment of a PCSK9 gene designates any portion of at least about 8 consecutive nucleotides of a sequence as disclosed above, preferably at least about 15, more preferably at least about 20 nucleotides, further preferably of at least 30 nucleotides. Fragments include all possible nucleotide length between 8 and 100 nucleotides, preferably between 15 and 100, more preferably between 20 and 100. Said fragment can be useful as primer or probe for identifying an alteration of the PCSK9 gene in a sample of a subject or for genotyping a PCSK9 polymorphism, preferably a polymorphism disclosed in Table 2. Said fragment can be a reagent of a diagnostic kit.

The alteration of the NARC-1 protein can be a substitution, a deletion or an addition of at least one amino acid. Preferably, said alteration is a substitution. More preferably, said substitution is selected from the group consisting of a substitution of the residue Serine at position 127 of SEQ ID No 2, a substitution of the residue Phenylalanine at position 216 of SEQ ID No 2 and a combination thereof. Still more preferably, said substitution is selected from the group consisting of a substitution of the residue Serine at position 127 of SEQ ID No 2 by an Arginine (S127R), a substitution of the residue Phenylalanine at position 216 of SEQ ID No 2 by a Leucine (F216L) and a combination thereof. In this respect, a specific object of this invention concerns a polypeptide sequence of SEQ ID No 2 or a polypeptide comprising a fragment of SEQ ID No 2, said polypeptide comprising either the residue Arginine at position 127 or the residue Leucine at position 216 or a combination thereof. The invention also concerns a polynucleotide encoding said altered NARC-1 protein.

A fragment of a NARC-1 protein designates any portion of at least about 8 consecutive amino acids of a sequence as disclosed above, preferably at least about 15, more preferably at least about 20 amino acids, further preferably of at least 30 amino acids. Fragments include all possible nucleotide length between 8 and 100 amino acids, preferably between 15 and 100, more preferably between 20 and 100. Said fragment can be useful for preparing antibodies.

The invention also relates to an antibody specific of a NARC-1 protein comprising an alteration according to the present invention. In a preferred embodiment, said alteration causes hypercholesterolemia, more particularly ADH, and/or lipid and lipoprotein metabolism disorders. More preferably, the invention relates to an antibody specific of a NARC-1 protein comprising a substitution of the residue Serine at position 127 of SEQ ID No 2 by an Arginine (S1127R) or a substitution of the residue Phenylalanine at position 216 of SEQ ID No 2 by a Leucine (F216L) or a combination thereof. Furthermore, the invention relates to an antibody specific of a NARC-1 protein comprising an alteration selected from the group consisting of an insertion of a residue Leucine at position 15 of SEQ ID No 2, a substitution of the residue Arginine at position 46 of SEQ ID No 2 by a Leucine (R46L), a substitution of the residue Alanine at position 53 of SEQ ID No 2 by a Valine (A53V), a substitution of the residue Isoleucine at position 474 of SEQ ID No 2 by a Valine (I474V), a substitution of the residue Glutamic acid at position 670 of SEQ ID No 2 by a Glycine (E670G) and a combination thereof. Moreover, the invention relates to an antibody specific of a NARC-1 protein comprising an alteration disclosed in Table 4, preferably selected from the group consisting of a substitution of the residue Tyrosine at position 78 of SEQ ID No 2, a substitution of the residue Valine at position 80 of SEQ ID No 2, a substitution of the residue. Leucine at position 82 of SEQ ID No 2, a substitution of the residues Valine at positions 79, 80 and 81 of SEQ ID No 2, a substitution of the residues Alanines at positions 102 and 103 of SEQ ID No 2, a substitution of the residues Valine at position 79, Lysine at position 83, and Leucine at position 112 of SEQ ID No 2, a substitution of the residue Methionine at position 126 of SEQ ID No 2, a substitution of the residue Proline at position 138 of SEQ ID No 2, a substitution of the residue Isoleucine at position 143 of SEQ ID No 2, a substitution of the residue Histidine at position 226 of SEQ ID No 2, and a substitution of the residue Asparagine at position 317 of SEQ ID No 2. More preferably, said alteration is selected from the group consisting of a substitution of the residue Tyrosine at position 78 of SEQ ID No 2 by an Alanine (Y78A), a substitution of the residue Valine at position 80 of SEQ ID No 2 by an Alanine or a Leucine (V80A or V80L), a substitution of the residue Leucine at position 82 of SEQ ID No 2 by an Alanine, a Valine or a Proline (L82A, L82V or L82P), a substitution of the residues Valine at positions 79, 80 and 81 of SEQ ID No 2 by an Arginine, an Arginine and a Leucine, respectively (V79R, V80R and V81L), a substitution of the residues Alanines at positions 102 and 103 of SEQ ID No 2 by Arginines (A102R and A103R), a substitution of the residues Valine at position 79, Lysine at position 83, and Leucine at position 112 of SEQ ID No 2 by an Isoleucine, a Methionine, a Proline, respectively (V79I, K83M and L112P), a substitution of the residue Methionine at position 126 of SEQ ID No 2 by an Alanine (M126A), a substitution of the residue Proline at position 138 of SEQ ID No 2 by a Tyrosine (P138Y), a substitution of the residue Isoleucine at position 143 of SEQ ID No 2 by a Proline (I143P), a substitution of the residue Histidine at position 226 of SEQ ID No 2 by an Alanine (H226A), and a substitution of the residue Asparagine at position 317 of SEQ ID No 2 by an Alanine (N317A). By "specific" is intended binds specifically the altered polypeptide and essentially does not bind specifically the wild-type polypeptide or the binding of the two forms can be discriminated.

Another object of the present invention is an altered PCSK9 gene having at least one nucleotide mutation at a position listed in Table 2. More particularly, the invention concerns an altered PCSK9 gene having the Leucine stretch modification, the corresponding encoded NARC-1 protein and the use thereof.

A further aspect of this invention resides in novel products for use in diagnosis, therapy or screening of hypercholesterolemia, more particularly ADH, and/or lipid and lipoprotein metabolism disorders. These products comprise nucleic acid molecules encoding a NARC-1 polypeptide according to the present invention, vectors comprising the same, recombinant host cells and expressed polypeptides.

A further object of this invention is a vector comprising a nucleic acid encoding a NARC-1 polypeptide comprising an alteration according to the present invention. The vector may be a cloning vector or, more preferably, an expression vector, i.e., a vector comprising regulatory sequences causing expression of a NARC-1 polypeptide from said vector in a competent host cell.

These vectors can be used to express a NARC-1 polypeptide according to the present invention in vitro, ex vivo or in vivo, to create transgenic or "Knock Out" non-human animals, to amplify the nucleic acids, to express antisense RNAs, etc.

The vectors of this invention typically comprise a NARC-1 coding sequence according to the present invention operably linked to regulatory sequences, e.g., a promoter, a polyA, etc. The term "operably linked" indicates that the coding and regulatory sequences are functionally associated so that the regulatory sequences cause expression (e.g., transcription) of the coding sequences. The vectors may further comprise one or several origins of replication and/or selectable markers. The promoter region may be homologous or heterologous with respect to the coding sequence, and provide for ubiquitous, constitutive, regulated and/or tissue specific expression, in any appropriate host cell, including for in vivo use. Examples of promoters include bacterial promoters (T7, pTAC, Trp promoter, etc.), viral promoters (LTR, TK, CMV-IE, etc.), mammalian gene promoters (albumin, PGK, etc), and the like.

The vector may be a plasmid, a virus, a cosmid, a phage, a BAC, a YAC, etc. Plasmid vectors may be prepared from commercially available vectors such as pBluescript, pUC, pBR, etc. Viral vectors may be produced from baculoviruses, retroviruses, adenoviruses, AAVs, etc., according to recombinant DNA techniques known in the art.

In this regard, a particular object of this invention resides in a recombinant virus encoding an altered NARC-1 polypeptide according to the present invention. The recombinant virus is preferably replication-defective, even more preferably selected from E1- and/or E4-defective adenoviruses, Gag-, pol- and/or env-defective retroviruses and Rep- and/or Cap-defective AAVs. Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO95/14785, WO96/22378, U.S. Pat. No. 5,882,877, U.S. Pat. No. 6,013,516, U.S. Pat. No. 4,861,719, U.S. Pat. No. 5,278,056 and WO94/19478.

A further object of the present invention resides in a recombinant host cell comprising a recombinant PCSK9 gene according to the present invention or a vector as defined above. Suitable host cells include, without limitation, prokaryotic cells (such as bacteria) and eukaryotic cells (such as yeast cells, mammalian cells, insect cells, plant cells, etc.). Specific examples include *E. coli*, *Kluyveromyces* or *Saccharomyces* yeasts, mammalian cell lines (e.g., Vero cells, CHO cells, 3T3 cells, COS cells, etc.) as well as primary or established mammalian cell cultures (e.g., produced from lymphoblasts, fibroblasts, embryonic cells, epithelial cells, nervous cells, adipocytes, etc.). More particularly, the invention contemplates liver and small intestine and cells thereof or derived thereof.

The present invention also relates to a method for producing a recombinant host cell expressing a NARC-1 polypeptide comprising an alteration according to the present invention, said method comprising (i) introducing in vitro or ex vivo into a competent host cell a recombinant nucleic acid or a vector as described above, (ii) culturing in vitro or ex vivo the recombinant host cells obtained and (iii), optionally, selecting the cells which express and/or secrete said NARC-1 polypeptide.

Such recombinant host cells can be used for the production of NARC-1 polypeptides according to the present invention, as well as for screening of active molecules, as described below. Such cells may also be used as a model system to study hypercholesterolemia, more particularly ADH, and/or lipid and lipoprotein metabolism disorders. These cells can be maintained in suitable culture media, such as DMEM, RPMI, HAM, etc., in any appropriate culture device (plate, flask, dish, tube, pouch, etc.).

Diagnosis

The invention now provides diagnosis methods based on a monitoring of alteration at the PCSK9 gene locus in a subject. Within the context of the present invention, the term "diagnosis" includes the detection, monitoring, dosing, comparison, etc., at various stages, including early, pre-symptomatic stages, and late stages, in adults, children and pre-birth. Diagnosis typically includes the prognosis, the assessment of a predisposition or risk of development, the characterization of a subject to define most appropriate treatment (pharmaco-genetics), etc.

A particular object of this invention resides in a method of detecting the presence of or predisposition to hypercholesterolemia, more particularly ADH, and/or lipid and lipoprotein metabolism disorders in a subject, the method comprising (i) providing a sample from the subject and (ii) detecting the presence of an alteration in the PCSK9 gene locus in said sample, the presence of said alteration is indicative of the presence of or predisposition to hypercholesterolemia, more particularly ADH, and/or lipid and lipoprotein metabolism disorders. Preferably, said alteration is a nucleotide substitution. More preferably, the invention concerns a method of detecting the presence of or predisposition to ADH.

A particular object of this invention resides in a method of detecting the presence of or predisposition to hypercholesterolemia, more particularly ADH, and/or lipid and lipoprotein metabolism disorders in a subject, the method comprising (i) providing a sample from the subject and (ii) detecting the presence of an alteration in the NARC-1 mRNA in said sample, the presence of said alteration is indicative of the presence of or predisposition to hypercholesterolemia, more particularly ADH, and/or lipid and lipoprotein metabolism disorders. Preferably, said alteration is a nucleotide substitution. More preferably, the invention concerns a method of detecting the presence of or predisposition to ADH.

An additional particular object of this invention resides in a method of detecting the presence of or predisposition to hypercholesterolemia, more particularly ADH, and/or lipid and lipoprotein metabolism disorders in a subject, the method comprising (i) providing a sample from the subject and (ii) detecting the presence of an alteration in the NARC-1 polypeptide in said sample, the presence of said alteration is indicative of the presence of or predisposition to hypercholesterolemia, more particularly ADH, and/or lipid and lipoprotein metabolism disorders. Preferably, said alteration is an amino acid substitution. More preferably, the invention concerns a method of detecting the presence of or predisposition to ADH.

An other particular object of this invention resides in a method of assessing the response of a subject to a treatment of hypercholesterolemia, more particularly ADH, and/or lipid and lipoprotein metabolism disorders, the method comprising (i) providing a sample from the subject and (ii) detecting the presence of an alteration in the PCSK9 gene locus, in the NARC-1 mRNA or in the NARC-1 polypeptide in said sample, the presence of said alteration is indicative of a particular response to said treatment. Preferably, said alteration is a nucleotide or amino acid substitution. More preferably, the invention concerns a method of assessing the response of a subject to a treatment of ADH.

A further object of the present invention resides in a method of detecting the presence of or predisposition to hypercholesterolemia, more particularly ADH, and/or lipid and lipoprotein metabolism disorders in a subject, the method comprising (i) providing a sample from the subject and (ii) detecting the presence of an alteration in the PCSK9 gene, the LDL receptor gene and/or the apolipoprotein B gene in said sample, the presence of said alteration is indicative of the presence of or predisposition to hypercholesterolemia, more particularly ADH, and/or lipid and lipoprotein metabolism disorders. Similarly, the alteration can also be detected at the protein level. More preferably, the invention concerns a method of detecting the presence of or predisposition to ADH.

An alteration in the gene may be any form of mutation(s), deletion(s), rearrangement(s) and/or insertions in the coding and/or non-coding region of the locus, alone or in various combination(s). Mutations more specifically include point mutations, as disclosed above. In a preferred embodiment of the present invention, the alteration is a nucleotide or amino acid substitution.

The detection of the presence of an altered PCSK9 gene or an altered NARC-1 mRNA sequence according to the present invention can be performed by sequencing all or part of the PCSK9 gene, polypeptide or RNA, by selective hybridisation or by selective amplification, for instance.

A more specific embodiment comprises detecting the presence of a polymorphism as disclosed in Table 2 in the PCSK9 gene sequence or NARC-1 mRNA of a subject. More particularly, the alteration of the PCSK9 gene locus is detected through an haplotype segregating with the mutation causing ADH, more preferably the haplotype (polymorphisms B (absence of insertion), H, I, M and U of Table 2).

Preferably, the alteration detected in the PCSK9 gene locus or NARC-1 mRNA is selected from the group consisting of a substitution of the nucleotide T at position 625 and 890 of SEQ ID No 1 and a combination thereof, more preferably a T→A substitution at position 625 of SEQ ID No 1, a T→C substitution at position 890 of SEQ ID No 1 and a combination thereof.

Alternatively, the alteration detected in the PCSK9 gene locus or NARC-1 mRNA can also be selected from the group consisting of a substitution of the nucleotide A at position 898 and a substitution of the nucleotide C at position 953 of SEQ ID No 1 and a combination thereof, more preferably a A→T substitution at position 898 of SEQ ID No 1, a C→T substitution at position 953 of SEQ ID No 1 and a combination thereof.

Preferably, the alteration detected in the NARC-1 protein is selected from the group consisting of a substitution of the residue Serine at position 127 of SEQ ID No 2, a substitution of the residue Phenylalanine at position 216 of SEQ ID No 2 and a combination thereof, more preferably a substitution of the residue Serine at position 127 of SEQ ID No 2 by an Arginine (S127R) or a substitution of the residue Phenylalanine at position 216 of SEQ ID No 2 by a Leucine (F216L) or a combination thereof.

Alternatively, the alteration detected in the NARC-1 protein can also be selected from the group consisting of a substitution of the residue Arginine at position 218 of SEQ ID No 2, a substitution of the residue Arginine at position 237 of SEQ ID No 2 and a combination thereof, more preferably a substitution of the residue Arginine at position 218 of SEQ ID No 2 by a Serine (R218S) or a substitution of the residue Arginine at position 237 of SEQ ID No 2 by a Tryptophane (R237W) or a combination thereof.

An object of the present invention resides in a method of detecting the presence of or predisposition to hypercholesterolemia, more particularly ADH, and/or lipid and lipoprotein metabolism disorders in a subject, the method comprising (i) providing a sample from the subject and (ii) detecting the presence of an altered NARC-1 RNA and/or polypeptide expression, the presence of said altered NARC-1 RNA and/or polypeptide expression is indicative of the presence of or predisposition to hypercholesterolemia, more particularly ADH, and/or lipid and lipoprotein metabolism disorders. More preferably, the invention concerns a method of detecting the presence of or predisposition to ADH.

An object of the present invention resides in a method of assessing the response of a subject to a treatment of hypercholesterolemia, more particularly ADH, and/or lipid and lipoprotein metabolism disorders in a subject, the method comprising (i) providing a sample from the subject and (ii) detecting the presence of an altered NARC-1 RNA and/or polypeptide expression, the presence of said altered NARC-1 RNA and/or polypeptide expression is indicative of a particular response to said treatment. More preferably, the invention concerns a method of detecting the presence of or predisposition to ADH.

ALTERED RNA expression includes the presence of an altered RNA sequence, the presence of an altered RNA splicing or processing, the presence of an altered quantity of RNA, etc. These may be detected by various techniques known in the art, including by sequencing all or part of the NARC-1 RNA or by selective hybridisation or selective amplification of all or part of said RNA, for instance.

Altered NARC-1 polypeptide expression includes the presence of an altered polypeptide sequence, the presence of an altered quantity of NARC-1 polypeptide, the presence of an altered tissue distribution, etc. These may be detected by various techniques known in the art, including by sequencing and/or binding to specific ligands (such as antibodies), for instance.

A further object of the present invention resides in a method of detecting the presence of or predisposition to hypercholesterolemia, more particularly ADH, and/or lipid and lipoprotein metabolism disorders in a subject, the method comprising (i) providing a sample from the subject and (ii) detecting the presence of an altered NARC-1 activity, the presence of said altered NARC-1 activity is indicative of the presence of or predisposition to hypercholesterolemia, more particularly ADH, and/or lipid and lipoprotein metabolism disorders. Preferably, said altered NARC-1 activity is a decreased NARC-1 activity. More preferably, the invention concerns a method of detecting the presence of or predisposition to ADH.

A further object of the present invention resides in a method of assessing the response of a subject to a treatment of hypercholesterolemia, more particularly ADH, and/or lipid and lipoprotein metabolism disorders in a subject, the method comprising (i) providing a sample from the subject and (ii) detecting the presence of an altered NARC-1 activity, the presence of said altered NARC-1 activity is indicative of a particular response to said treatment. Preferably, said altered NARC-1 activity is a decreased NARC-1 activity. More preferably, the invention concerns a method of detecting the presence of or predisposition to ADH.

An object of the present invention resides in a method of genotyping at least one polymorphism of the PCSK9 gene, preferably listed in Table 2, comprising (i) providing a sample from the subject and (ii) determining the identity of the allele of said polymorphism in said sample. Preferably, the identity of the allele is determined by performing a hydridization assay, a sequencing assay, a microsequencing assay, an allele-specific amplification assay.

The present invention also relates to a method of determining the existence of an association between a polymorphism and a disease or disorder, comprising the steps of: (i) genotyping at least one polymorphism of the PCSK9 gene, preferably one listed in Table 2, in a population having said disease or disorder; (ii) genotyping said polymorphism: in a control population; and, (iii) determining whether a statistically significant association exists between said disease or disorder and said polymorphism.

As indicated above, various techniques known in the art may be used to detect or quantify altered PCSK9 gene or RNA expression or sequence, including sequencing, hybridisation, amplification and/or binding to specific ligands (such as antibodies). Other suitable methods include allele-specific oligonucleotide (ASO), allele-specific amplification, Southern blot (for DNAs), Northern blot (for RNAs), single-stranded conformation analysis (SSCA), PFGE, fluorescent in situ hybridization (FISH), gel migration, clamped denaturing gel electrophoresis, heteroduplex analysis, RNase protection, chemical mismatch cleavage, ELISA, radio-immunoassays (RIA) and immuno-enzymatic assays (EEMA).

Some of these approaches (e.g., SSCA and CGGE) are based on a change in electrophoretic mobility of the nucleic acids, as a result of the presence of an altered sequence. According to these techniques, the altered sequence is visualized by a shift in mobility on gels. The fragments may then be sequenced to confirm the alteration.

Some others are based on specific hybridization between nucleic acids from the subject and a probe specific for wild-type or altered PCSK9 gene or RNA. The probe may be in suspension or immobilized on a substrate. The probe is typically labelled to facilitate detection of hybrids. By "specific hybridization" is intended a hybridization under stringent conditions.

Some of these approaches are particularly suited for assessing a polypeptide sequence or expression level, such as Northern blot, ELISA and RIA. These latter require the use of a ligand specific for the polypeptide, more preferably of a specific antibody.

Sequencing can be carried out using techniques well known in the art, using automatic sequencers. The sequencing may be performed on the complete PCSK9 gene or, more preferably, on specific domains thereof, typically those known or suspected to carry deleterious mutations or other alterations.

Amplification may be performed according to various techniques known in the art, such as by polymerase chain reaction (PCR), ligase chain reaction (LCR), strand displacement amplification (SDA) and nucleic acid sequence based amplification (NASBA). These techniques can be performed using commercially available reagents and protocols. Preferred techniques use allele-specific PCR or PCR-SSCP. Amplification usually requires the use of specific nucleic acid primers, to initiate the reaction.

In this regard, a particular object of this invention resides in a nucleic acid primer useful for amplifying sequences from the PCSK9 gene or locus. Such primers are preferably complementary to, and hybridize specifically under stringent conditions to nucleic acid sequences in the PCSK9 gene locus. Particular primers are able to specifically hybridise under stringent conditions with a portion of the PCSK9 gene locus that flank a target region of said locus, said region comprising an alteration according to the present invention, more particularly a substitution of the nucleotide T at position 625 and/or 890 of SEQ ID No 1 or a polymorphism listed in Table 2, preferably said target region being altered in certain subjects having ADH.

A aspect of this invention includes a pair of nucleic acid primers, wherein said pair comprises a sense and a reverse primers, and wherein said sense and a reverse primers specifically amplify a PCSK9 gene or RNA or a target region thereof, said region comprising an alteration according to the present invention, more particularly a substitution of the nucleotide T at position 625 and/or 890 of SEQ ID No 1 or a polymorphism listed in Table 2, preferably said target region being altered in certain subjects having hypercholesterolemia, more particularly ADH and/or lipid and lipoprotein metabolism disorders.

In a more specific embodiment, the invention relates to a nucleic acid primer, wherein said primer is complementary to and hybridizes specifically under stringent conditions to a portion of a PCSK9 coding sequence (e.g., gene or RNA), wherein said portion comprising an alteration according to the present invention, more particularly a substitution of the nucleotide T at position 625 and/or 890 of SEQ ID No 1 or a polymorphism listed in Table 2. Preferably, said alteration is present in certain subjects having hypercholesterolemia, more particularly ADH and/or lipid and lipoprotein metabolism disorders. In this regard, particular primers of this invention are specific for altered sequences in a PCSK9 gene or RNA. By using such primers, the detection of an amplification product indicates the presence of an alteration in the PCSK9 gene locus. In contrast, the absence of amplification product indicates that the specific alteration is not present in the sample. More preferably, said primers comprises the nucleotide at position 625 and/or 890 of SEQ ID No 1, or the nucleotide at position 5158 and/or 13539 of SEQ ID No 3. Alternatively, said primers comprises one polymorphism listed in Table 2.

Typical primers of this invention are single-stranded nucleic acid molecules of about 5 to 60 nucleotides in length, more preferably of about 8 to about 25 nucleotides in length. The sequence can be derived directly from the sequence of the PCSK9 gene locus. Perfect complementarity is preferred, to ensure high specificity. However, certain mismatch may be tolerated.

A particular detection technique involves the use of a nucleic acid probe specific for wild-type or altered PCSK9 gene or RNA, followed by the detection of the presence of a hybrid. The probe may be in suspension or immobilized on a substrate or support (as in nucleic acid array or chips technologies). The probe is typically labelled to facilitate detection of hybrids.

In this regard, a particular embodiment of this invention comprises contacting the sample from the subject with a nucleic acid probe specific for an altered PCSK9 gene locus, and assessing the formation of an hybrid. In a particular, preferred embodiment, the method comprises contacting simultaneously the sample with a set of probes that are specific, respectively, for wild type PCSK9 gene locus and for various altered forms thereof. In this embodiment, it is possible to detect directly the presence of various forms of alterations in the PCSK9 gene locus in the sample. Also, various samples from various subjects may be treated in parallel.

A further particular object of this invention resides in a nucleic acid probe specific for a PCSK9 gene or RNA. Within the context of this invention, a probe refers to a polynucleotide sequence which is complementary to and capable of specific hybridisation under stringent conditions with a (target portion of a) PCSK9 gene or RNA, and which is suitable for detecting polynucleotide polymorphisms, preferably the polymorphism associated with PCSK9 alleles which predispose to or are associated with ADH. Probes are preferably perfectly complementary to the PCSK9 gene, RNA, or target portion thereof. Probes typically comprise single-stranded nucleic acids of between 8 to 1000 nucleotides in length, for instance of between 10 and 800, more preferably of between 15 and 700, typically of between 20 and 500. It should be understood that longer probes may be used as well. A preferred probe of this invention is a single stranded nucleic acid molecule of between 8 to 500 nucleotides in length, which can specifically hybridise under stringent conditions to a region of a PCSK9 gene or RNA that carries an alteration.

A specific embodiment of this invention is a nucleic acid probe specific for an altered (e.g., a mutated) PCSK9 gene or RNA, i.e., a nucleic acid probe that specifically hybridises under stringent conditions to said altered PCSK9 gene or RNA and essentially does not hybridise under stringent conditions to a PCSK9 gene or RNA lacking said alteration. Specificity indicates that hybridisation to the target sequence generates a specific signal which can be distinguished from the signal generated through non-specific hybridisation. Perfectly complementary sequences are preferred to design probes according to this invention. It should be understood, however, that certain mismatch may be tolerated, as long as the specific signal may be distinguished from non-specific hybridisation.

Particular examples of such probes are nucleic acid sequences complementary to a target portion of the PCSK9 gene or RNA carrying the nucleotide at position 625 and/or 890 of SEQ ID No 1, the nucleotide at position 5158 and/or 13539 of SEQ ID No 3, a polymorphism listed in Table 2, or a mutation disclosed in Table 4.

The sequence of the probes can be derived from the sequences of the PCSK9 gene and RNA as provided in the present application. Nucleotide substitutions may be performed, as well as chemical modifications of the probe. Such chemical modifications may be accomplished to increase the stability of hybrids (e.g., intercalating groups) or to label the probe. Typical examples of labels include, without limitation, radioactivity, fluorescence, luminescence, enzymatic labelling, etc.

As indicated above, alteration in the PCSK9 gene locus may also be detected by screening for alteration(s) in NARC-1 polypeptide sequence or expression levels. In this regard, a specific embodiment of this invention comprises contacting the sample with a ligand specific for an altered NARC-1 polypeptide and determining the formation of a complex.

Different types of ligands may be used, such as specific antibodies. In a specific embodiment, the sample is contacted with an antibody specific for an altered NARC-1 polypeptide and the formation of an immune complex is determined. Various methods for detecting an immune complex can be used, such as ELISA, radio-immunoassays (RIA) and immuno-enzymatic assays (IEMA).

In a specific embodiment, the method comprises contacting a sample from the subject with (a support coated with) an antibody specific for an altered form of a NARC-1 polypeptide, and determining the presence of an immune complex. In a particular embodiment, the sample may be contacted simultaneously, or in parallel, or sequentially, with various (supports coated with) antibodies specific for different forms of a NARC-1 polypeptide, such as a wild-type and various altered forms thereof.

Particular examples of such specific ligands are antibodies specific for altered NARC-1 polypeptide sequence resulting from any mutation in position 127 and/or 216, more particularly a substitution of the residue Serine at position 127 by an Arginine (S127R) or a substitution of the residue Phenylalanine at position 216 by a Leucine (F216L) or any combination of those mutations.

The invention also relates to a diagnostic kit comprising products and reagents for detecting in a sample from a subject the presence of an alteration in the PCSK9 gene or in the NARC-1 protein, in the NARC-1 RNA or polypeptide expression, and/or in NARC-1 activity. Optionally, said diagnostic kit further comprises reagents for detecting in a sample from a subject the presence of an alteration in the LDL receptor and/or the apolipoprotein B. Said diagnostic kit according to the present invention comprises any primer, any pair of primers, any nucleic acid probe and/or any antibody described in the present invention. Said diagnostic kit according to the present invention can further comprise reagents and/or protocols for performing a hybridization, amplification or antigen-antibody immune reaction.

Screening

The present invention also provides novel targets and methods for the screening of drug candidates or leads. Such drug candidates or leads are useful for developing a treatment against hypercholesterolemia, more particularly ADH, lipid and lipoprotein metabolism disorders, atherosclerosis, and/or CVD. Preferably, such drug candidates or leads are useful for developing a treatment against ADH. The methods include binding assays and/or functional assays, and may be performed in vitro, in cell systems, in animals, etc. Functional assays comprise, but are not limited to, the cleavage of a substrate. The in vitro assays, cell-based assays and animal-based assays involve a NARC-1 protein, preferably a NARC-1 protein comprising an alteration according to the present invention. Optionally, said assays comprise a control with a natural NARC-1 protein.

For cell systems, cells can be native, i.e., cells that normally express the NARC-1 polypeptide, as a biopsy or expanded in cell culture. Preferably, these native cells are derived from liver or small intestine. Alternatively, cells are recombinant host cells expressing NARC-1, more particularly a NARC-1 protein comprising an alteration according to the present invention.

The invention relates to methods for identifying of the target proteins of the NARC-1 protein, preferably a NARC-1 protein comprising an alteration according to the present invention.

The invention relates to methods for screening of compounds that modulate the NARC-1 activity. Such compounds, for example, can increase or decrease affinity and/or rate of binding of the NARC-1 protein to the substrate, compete with substrate for binding to the NARC-1 protein, or displace substrate bound to the NARC-1 protein. Preferably, the invention concerns methods for screening of compounds that increase or restore the natural NARC-1 activity. By "natural" NARC-1 activity is intended the activity of the wild-type NARC-1 protein. Furthermore, the invention concerns methods for screening of compounds that inhibit the activity of the altered NARC-1 comprising an alteration changing the substrate specificity and, thereby generating new substrates. Said compounds are able to block the activity of the altered NARC-1 for its new substrate.

Therefore, the present invention concerns a method of selecting biologically active compounds, said method comprising contacting a test compound with an altered PCSK9 gene or an altered NARC-1 protein or fragment thereof of at least 15 consecutive residues comprising an alteration, wherein the alteration reduces, modifies, or abolishes the activity of NARC-1, and determining the ability of said test compound to modulate the expression and/or activity of said gene or protein or fragment.

A particular object of this invention resides in a method of selecting biologically active compounds, said method comprising contacting in vitro a test compound with a PCSK9 gene or NARC-1 polypeptide, preferably a PCSK9 gene or a NARC-1 polypeptide, or a fragment thereof of at least 15 consecutive residues, comprising an alteration according to the present invention, and determining the ability of said test compound to bind said PCSK9 gene or NARC-1 polypeptide. Binding to said gene or polypeptide provides an indication as to the ability of the compound to modulate the activity of said target, and thus to affect a pathway leading to hypercholesterolemia, more particularly ADH, and lipid and/or lipoprotein metabolism disorders in a subject. In a preferred embodiment, the method comprises contacting in vitro a test compound with a NARC-1 polypeptide or a fragment thereof, preferably a NARC-1 polypeptide or a fragment thereof comprising an alteration according to the present invention, and determining the ability of said test compound to bind said NARC-1 polypeptide or fragment. The fragment preferably comprises a substrate-binding site of the NARC-1 polypeptide.

A particular object of this invention resides in a method of selecting compounds active against hypercholesterolemia, more particularly ADH, and/or lipid and lipoprotein metabolism disorders, said method comprising contacting in vitro a test compound with a NARC-1 polypeptide or a fragment thereof of at least 15 consecutive residues, preferably a NARC-1 polypeptide or a fragment thereof comprising an alteration according to the present invention, and determining the ability of said test compound to bind said NARC-1 polypeptide or fragment thereof. The NARC-1 polypeptide or fragment thereof may be used in essentially pure form, in suspension, or immobilized on a support.

In a further particular embodiment, the method comprises contacting a recombinant host cell expressing NARC-1 polypeptide, preferably a NARC-1 polypeptide comprising an alteration according to the present invention, with a test compound, and determining the ability of said test compound to bind said NARC-1 polypeptide and/or to modulate the activity of NARC-1 polypeptide.

The determination of binding may be performed by various techniques, such as by labelling of the test compound, by competition with a labelled reference ligand, two-hybrid Screening Assay, etc. Modulation of activity includes, without limitation, the inhibition or activation of the autocatalytic processing of pro-NARC-1, and/or the inhibition or activation of the substrate cleavage, more particularly a synthetic substrate comprising a zymogenic processing site.

A further object of this invention resides in a method of selecting biologically active compounds, said method comprising contacting in vitro a test compound with a NARC-1 polypeptide, preferably a NARC-1 polypeptide comprising an alteration according to the present invention, and determining the ability of said test compound to modulate the activity of said NARC-1 polypeptide.

A further object of this invention resides in a method of selecting biologically active compounds, said method comprising contacting in vitro a test compound with a PCSK9 gene, preferably a PCSK9 gene comprising an alteration according to the present invention, and determining the ability of said test compound to modulate the expression of said PCSK9 gene.

The invention also concerns methods of selecting biologically active compounds using a non-human transgenic animals expressing a NARC-1 protein, preferably a NARC-1 protein comprising an alteration according to the present invention. Optionally, said non-human transgenic animals can be homozygote or heterozygote for the altered PCSK9 gene. Said methods comprise (i) administrating a test compound to said non-human transgenic animal, and (ii) determining the ability of said test compound to modulate the NARC-1 activity. Said NARC-1 activity can be assessed by determining the plasmatic concentration of cholesterol and/or lipoparticules (VLDL, IDL, LDL), by determining the plasmatic enzymatic activity of NARC-1, by analyzing some tissues (liver, small intestine), by determining the lipoprotein kinetics. The enzymatic activity of NARC-1 can be determined with synthetic substrate, such as described in Seidah et al (2003).

The above screening assays may be performed in any suitable device, such as plates, tubes, dishes, flasks, etc. Typically, the assay is performed in multi-wells plates. Several test compounds can be assayed in parallel.

Furthermore, the test compound may be of various origin, nature and composition. It may be any organic or inorganic substance, such as a lipid, peptide, polypeptide, nucleic acid, small molecule, etc., in isolated or in mixture with other substances. The compounds may be all or part of a combinatorial library of products, for instance. The test compounds can be an antisense or an RNAi. The test compounds can be competitive or suicide substrates. By "suicide substate" is intended a compounds that, after binding NARC-1 protein, the reactive group forms an irreversible bond with NARC-1 rendering it inactive.

Therapy

The invention contemplates methods of treatment of hypercholesterolemia, more particularly ADH, lipid and lipoprotein metabolism disorders, atherosclerosis and/or CVD. Preferably, the invention relates to methods of treatment of hypercholesterolemia, more particularly ADH, and/or lipid and lipoprotein metabolism disorders due to an alteration of NARC-1 protein.

The invention also relates to a method of treating or preventing hypercholesterolemia, more particularly ADH, lipid and lipoprotein metabolism disorders, atherosclerosis and/or CVD in a subject, the method comprising administering to said subject a functional (e.g., wild-type) NARC-1 polypeptide or a nucleic acid encoding the same. More preferably, the invention concerns a method of treating or preventing ADH.

The invention concerns the use of a functional NARC-1 polypeptide or a nucleic acid encoding the same, in the manufacture of a pharmaceutical composition for treating or preventing hypercholesterolemia, more particularly ADH, lipid and lipoprotein metabolism disorders, atherosclerosis and/or CVD in a subject. More preferably, the invention concerns a pharmaceutical composition for treating or preventing ADH.

The invention also relates to a method of treating or preventing hypercholesterolemia, more particularly ADH, lipid and lipoprotein metabolism disorders, atherosclerosis and/or CVD in a subject, the method comprising administering to said subject a compound that modulates NARC-1 expression and/or activity. More preferably, the invention concerns a method of treating or preventing ADH. The invention further relates to a pharmaceutical composition comprising a compound that modulates NARC-1 expression and/or activity.

The invention relates, generally, to the use of a compound that modulates NARC-1 expression and/or activity in the manufacture of a pharmaceutical composition for treating or preventing hypercholesterolemia, more particularly ADH, lipid and lipoprotein metabolism disorders, atherosclerosis and/or CVD in a subject. More preferably, the invention concerns a pharmaceutical composition for treating or preventing ADH.

The present invention demonstrates the causal link between hypercholesterolemia, more particularly ADH, and an alteration of the PCSK9 gene locus. The invention thus provides a novel target of therapeutic intervention. Various approaches can be contemplated to restore or modulate the NARC-1 activity or function, more particularly normal NARC-1 activity or function, in a subject, particularly those carrying an altered PCSK9 gene locus. Supplying wild-type function to such subject is expected to suppress phenotypic expression of hypercholesterolemia, more particularly ADH, in a pathological cell or organism. The supply of such function can be accomplished through gene or protein therapy, or by administering compounds that modulate NARC-1 activity.

If the alteration of NARC-1 protein leads to a decrease or loss of NARC-1 activity, the treatment consists in administering a biologically active compound which increases or restores the NARC-1 activity. Said biologically active compound can be a natural NARC-1 protein. Alternatively, said compound can be an activator of the NARC-1 protein. Said compound can also increase the expression of NARC-1 protein.

If the alteration of NARC-1 protein leads to a new specificity for a substrate, the treatment consists in administrating a biologically active compound which inhibits the activity of the altered NARC-1 protein. Said compound can decrease the expression of NARC-1 protein. For example, such compounds can be an antisens or an RNAi of PCSK9 gene comprising the alteration causing ADH. Alternatively, said compound can be an inhibitor of the altered NARC-1 protein. Said compound can compete with the substrate or can be a suicide substrate.

Further aspects and advantages of the present invention will be disclosed in the following experimental section, which should be regarded as illustrative and not limiting the scope of the present invention. The references cited in the present application are all incorporated herein by reference.

EXAMPLES

The inventors mapped a third locus HCHOLA3 at 1p32 and now report two mutations in the PCSK9 gene causing ADH. PCSK9 encodes NARC-1 (neural apoptosis regulated convertase). Its mutations lead to reduced activation of the enzyme. Lipoprotein kinetics in probands revealed an overproduction of apoB100-rich particles showing that the pathogenic origin of the disease is hepatic. In conclusion, NARC-1 is a newly identified human subtilase that contributes to cholesterol homeostasis and is the first example of a dominant disease associated with a defect in a member of the large subtilase family. To identify the HCHOLA3 locus (formerly FH3), that the inventors mapped (Varret et al, 1999) to 1p34.1-p32 (OMIM603776) and was confirmed by Hunt et al. in a large Utah kindred (Hunt et al, 2000), the inventors performed positional cloning using the originally linked family and 23 French families in which the implication of the LDLR and APOB genes had been excluded.

Family HC92 was identified through the proband (HC92-II-7) who belongs to a multiplex ADH pedigree from which twenty-nine family members were sampled and tested in parametric linkage analyses. In the reduced pedigree studied in the linkage analysis, 12 subjects presented with total cholesterol levels above the 97.5$^{th}$ percentile when compared with other French individuals matched by age and sex (Steinmetz, 1990) (mean total cholesterol: 3.63 g/L±0.68, mean LDL-cholesterol: 2.87±0.72 g/L). The inventors excluded linkage to the LDLR and APOB genes [lod scores at −14.05 and −10.01 (θ=0.0), respectively]. The family was genotyped for 8 Genethon markers in the 1p34-p32 region (FIG. 1). The inventors obtained highly significant lod scores with a maximum of 4.26 (θ=0.0) at D1S2742 that reached 4.80 in the multipoint analyses (Table 1, FIG. 3a). Haplotype analysis identified a 5.9 Mb critical interval between D1S231 and D1S2890. The critical interval that our team had previously reported in the HC2 family (Varret et al, 1999) was between markers D1S472 and D1S211, thus more distal. Reexamination of haplotype data (FIG. 2) showed that all affected subjects of the HC2 family also shared the same haplotype between markers D1S2722 and D1S2890 except HC2-II-5. This "affected" subject presented a recombinational event at D1S211 thus providing the centromeric boundary of the region described in 1999. Therefore all family members were reinvestigated. HC2-II-5 (who refuses treatment) was the only subject who showed a significant variation (a marked elevation of triglycerides) and thus no longer conforms with the inclusion criteria.

The inventors established the physical map of the candidate region between D1S197 and D1S2890 covered by 82 overlapping BAC sequences released from the Human Genome Project. The region between D1S197 and D1S2890 contains 41 genes among which 8 encode interesting functional candidates with respect to lipid metabolism: EPS 15 (Epidermal growth factor receptor pathway substrate-15), OSBPL9 (Oxysterol binding protein-like 9), SCP2 (Sterol carrier protein 2), LRP8 (Low density lipoprotein receptor-related protein 8), DHCR24 (24-dehydrocholesterol reductase), PRKAA2 (Protein kinase, AMP-activated, alpha 2 catalytic subunit), DAB1 (Disabled homolog 1) and PCSK9 (encoding NARC-1). This Neural Apoptosis Regulated Convertase 1 is a novel putative proprotein convertase (PC) belonging to the subtilase subfamily (Seidah et al, 2003). A related protein is the subtilisin kexin isoenzyme-1 (SKI-1)/site-1-protease (S1P) known to play a key role in cholesterol homeostasis through the processing of the sterol regulatory element-binding proteins (SREBPs) (Brown & Goldstein, 1999; Elagoz et al, 2002). The cDNA spans 3617 bp encoding a 692 amino acid protein. NARC-1 was mapped to 1 p33-p34.3. The inventors precisely localized its cDNA using the Blast program (URL ncbi.nlm.nih.gov/BLAST/) in the HCHOLA3 interval as follows: tel-D1S231-D1S2661-D1S417-D1S2652-PCSK9-D1S475-D1S200-D1S2742-cen.

Figure 3B:
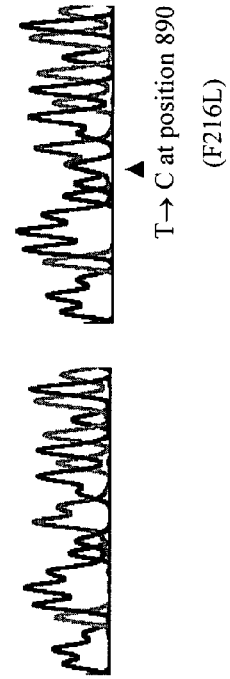
Figure 3C:
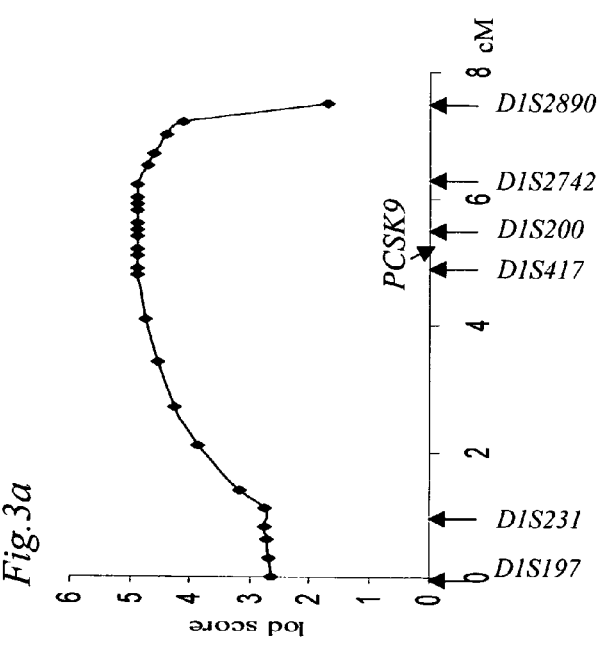

Systematic bidirectional sequencing of the 125 exons of the first seven candidates revealed no mutation in probands. By sequencing the 12 exons of PCSK9 the inventors identified in family HC92 a T→A substitution in exon 2 at nucleotide 625 predicting a substitution at codon 127 of Arginine for the conserved Serine (S127R), thereby creating a MnII cleavage site (FIG. 3b, FIG. 4). HC92 family members and 100 controls were tested for the substitution. It was absent in the 200 control chromosomes indicating that it is not a polymorphism. It was found in the 12 affected family members and in subject HC92-IV-3 who has a total cholesterol level in the 90$^{th}$ percentile when compared to other French individuals matched by age and sex. Thus, the penetrance in the family is estimated at 0.94. Interestingly, the S127R mutation was also found in the proband of HC2 and cosegregated with the disease in the family except in subject HC2-II-5, confirming that he had been misclassified in the linkage analyses previously reported (Varret et al, 1999). To assess the possible recurrence of this mutation, the inventors tested 5 intragenic polymorphic markers that the inventors had identified in PCSK9 (4 SNPs and a GCT repeat) in both families. The same haplotype segregated with the S127 R mutation in both the HC2 and the HC92 family: (Polymorphisms B (absence of insertion), H, I, M, and U) (Tables 2 and 3). Furthermore, a unique haplotype was also obtained for the extragenic markers surrounding PCSK9 (D1S2661, D1S417, D1S475, D1S200 and D1S2742) in both families. These results show that despite the absence of records and different geographical origins, the families share a common ancestor. The possibility of a French founder effect was ruled out since the mutation was not found in 22 other French ADH probands.

Figure 3D:
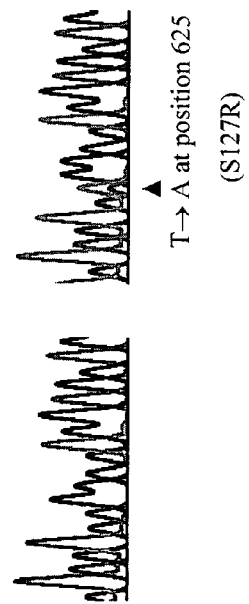

Through systematic bidirectional sequencing of the ~12 exons of the PCSK9 gene in 22 ADH probands, a second mutation (F216L) was identified in the proband of the HC60 family (FIG. 2c) who died from myocardial infarction at 49 y.o (FIG. 3d, FIG. 4). This mutation segregated with the ADH phenotype in the family and was not found in 200 control chromosomes. No major rearrangement was found in any of the probands by Southern blot (data not shown). Thus, mutations in PCSK9 have been found in 12.5% of the ADH families tested.

The inventors also identified 25 polymorphisms present in different probands and on control chromosomes from subjects with normal cholesterol levels (Table 2). These variations and their respective frequencies in the French population are listed in Table 2. It should be noted that none of these polymorphisms give rise to new donor or acceptor splice sites (score calculated according to Senaphthy et al.) (Senaphty et al, 1990; Shapiro & Senaphthy, 1987).

In order to unravel at the molecular level the consequences of the S127R and F216L mutations, the inventors introduced them in the human PCSK9 cDNA (Seidah et al., 2003). The inventors also obtained four other mutants, namely S127A, S127P, 15_16insL (polymorphic variant where an extra leucine is added in the signal peptide hydrophobic stretch) and the active site mutant H226A (Seidah et al., 2003). The cDNAs encoding wild type (WT) NARC-1 and its mutants containing a C-terminal V5 epitope, were transiently transfected in HEK293 cells. A 4 h pulse with $^{35}$S-labelled Met and Cys was followed by immunoprecipitation of the cell lysates and the media with a V5 mAb (Seidah et al., 2003). The inventors have previously shown that proNARC-1 is synthesized as a 72 kDa precursor that undergoes two zymogen cleavage events. The first one is rapid and occurs in the endoplasmic reticulum (ER) at the YVVVL$_{82}\downarrow$ site, giving rise to the 63-65 kDa N1 product and the 14 kDa prosegment (pro). The second one occurs with much lower efficacy at the putative PHVDY$_{142}\downarrow$ site and gives rise to the presumably active 58 kDa N2 enzyme (Brown & Goldstein, 1999). By STORM quantitation the inventors estimate that both S127R and F216L mutations lead to ~3-fold lower levels of N2. In addition, the secreted level of N1 was about 2-fold lower for the S127R mutant. Interestingly, while the S127A mutant shows a similar behavior, the S127P resembles WT. Finally, the 15_16insL allelic variant seems to give rise to a ~2-fold higher percentage of N1 and N2 products, suggesting that more active NARC-1 is produced.

The inventors have identified a new gene implicated in ADH by positional cloning. Linkage analyses were performed on two large French pedigrees: HC92 and HC2 in which the implication of the LDLR and APOB genes had been excluded. A maximum lod score of 4.26 was obtained for D1S2742 in family HC92. Haplotype analysis restricted the region of linkage to a 5.9 Mb interval between markers D1S231 and D1S2890 at 1p32. Our team had previously reported the localization of HCHOLA3 at 1p32-p34.1 by linkage analysis performed on the HC2 family (Varret et al, 1999). In this family, the critical interval was flanked by markers D1S472 and D1S211 and was thus more distal as compared to the one identified with the HC92 family. Reexamination of haplotype data showed that all affected subjects of the HC2 family also shared the same haplotype between markers D1S2722 and D1S2890 except (HC2-II-5). This "affected" subject presented a recombinational event at D1S211 thus providing the centromeric boundary of the region described in 1999. Therefore (HC2-II-5) was reinvestigated. The new lipid measurements showed the same elevated cholesterol but also marked elevation of triglycerides. This alteration can be explained by recent knowledge of a notable alcohol intake that presently prohibits proper assessment of the subject's status with respect to the family trait. Identification of the S127R PCSK9 gene mutation in all other affected members of the HC2 family and its absence in (HC2-II-5) confirmed that he had been misclassified for the genetic analyses. Identification of the S127R PCSK9 gene mutation in the HC92 family also helped to clarify the genetic status of the 8 children that had been sampled but not included in the linkage analyses. These results comforted the conservative approach that the inventors had chosen (total cholesterol above the 97.5$^{th}$ percentile when compared with sex- and age-matched French population) and that also allowed for reduced penetrance. This last parameter was confirmed since the S127R PCSK9 gene mutation was identified in (HC92-IV-3) who has a total cholesterol level in the 90$^{th}$ percentile (when compared to other French individuals matched by age and sex), and had higher cholesterol levels when compared to the levels of his non-affected sisters (2.5$^{th}$ percentile for HC92-IV-1 and 30$^{th}$ percentile for HC92-IV-2). Thus, the penetrance can now be estimated at 0.94 in the family when considering the inclusion criteria that were applied. This characteristic of a PCSK9 gene mutation is also found with LDLR gene mutations (Hobbs et al, 1989; Sass et al, 1995) and more generally accounts for the variability of the hypercholesterolemic phenotype (evaluated by common clinical and biological criteria) that can be due to the effect of environmental factors or of modifier genes.

Haplotype analysis showed that a unique haplotype segregated with the S127R mutation in both the HC92 and HC2 families. Therefore, it can be assumed that despite the absence of records and different geographical origins, the families share a common ancestor. The possibility of a French founder effect can be ruled out since the mutation was not found in a total of 22 other French probands (data not shown).

NARC-1 is a novel convertase recently cloned by two pharmaceuticals companies (NARC-1, Millenium Pharmaceuticals and LP251, Eli Lilly). It was first identified via the cloning of cDNAs upregulated following apoptosis induced by serum deprivation in primary cerebellar neurons. NARC-1 was more precisely characterized recently by Seidah et al. who used short conserved segments of the SKI-1 catalytic subunit as baits and the Protein Blast program to identify this convertase in a patented database (Seidah et al, 2003). It is synthesized as a soluble zymogen that undergoes autocatalytic intramolecular processing in the endoplasmic reticulum (ER) at the primary cleavage site YVVVL↓KEE$^{85}$ indicative of the enzymatic specificity (Seidah et al, 2003) of NARC-1. Prosegment cleavage is necessary for NARC-1 exit from the ER. The S127R mutation resides between the primary and putative secondary zymogen processing sites of proNARC-1, while F216L is located close to the active site (H226). Notably, the S127R mutation creates an RGD site that may be involved in integrin binding (Ruoslahti, 1996).

While only the S127R mutant causes reduction in the secreted level of N1, both the S127R and the F216L mutations result in reduced production of the enzymatically active N2. Furthermore, the kinetics of VLDL, IDL and LDL apo B100 performed in ADH subjects carrying the S127R mutation showed an overproduction from the liver of apo B100-rich lipoproteins. Thus, the dominance of the disease shows that NARC-1 is a rate-limiting enzyme involved in cholesterol homeostasis in the liver. Although most enzymopathies are recessively inherited, dominance is reported in some highly regulated or tissue specific enzymes. This is observed in two types of porphyria: AIP (acute intermittent porphyria) (Desnick et al, 1985) and PCT (porphyria cutanea tarda) (Felsher et al, 1982), that are caused by a porphobilinogen deaminase and uroporphyrinogen decarboxylase deficiency, respectively. However, contrary to porphyria, PCSK9 gene defects seem highly penetrant. NARC-1 belongs to the 9-membered mammalian subtilase family in which only one other member was known to carry a disease-causing mutation: a compound heterozygosity in the PC1 gene results in obesity and endocrinopathy due to impaired prohormone processing (MIM 162150). However, heterozygosity for one of the mutations is silent thus suggesting a recessive transmission (Jackson et al, 1997). Although PCs activate a wide variety of proteins, it is notable that none of them was linked so far to a dominant human disease. NARC-1 is thus unique in this respect and may lead to the discovery of others.

While the related convertase SKI-1/S1P plays a key role in regulating cholesterol and fatty acid homeostasis through the processing of SREBP1 and SREBP2, the precise implication of NARC-1 in cholesterol homeostasis is still under investigation. Interestingly, NARC-1 is mainly expressed in the liver and small intestine both of which play key roles in cholesterol synthesis and regulation (Seidah et al, 2003). Since apo B100 levels are regulated post-translationally (Bostrom et al, 1988), it is possible that NARC-1 could inactivate apo B100 and hence decrease the level of LDL. Indeed, a putative site LIEIGL↓EGK$^{668}$ of apo B100 is proposed which would respect the primary and secondary structure requirements of NARC-1 processing selectivity (Seidah et al, 2003). This may thus explain the reported ~70 kDa form of apo B100 that is observed to occur under stressful cellular conditions (Cavallo et al, 1999).

The crucial role of NARC-1 is revealed by the hypercholesterolemia that occurs when the gene is mutated resulting in a decreased NARC-1 activation. The identification of NARC-1 substrate(s) will help to elucidate novel disease mechanisms and constitute a target(s) for new intervention strategies to limit elevation of LDL particles and prevent morbidity and mortality from premature atherosclerosis.

Methods

Family Recruitment

The French hypercholesterolemic families were recruited through the 8 lipid clinics of the National Network for ADH ("Réseau National de Recherche sur les Hypercholestérolémies Familiales"). Probands were ascertained among consecutive patients of the clinics. Inclusion criteria for probands were: total cholesterol above the 97.5$^{th}$ percentile when compared with sex- and age-matched French population (Steinmetz, 1990), LDL cholesterol above 1.9 g/L or 1.6 g/L for children, triglycerides below 1.5 g/L, personal or documented familial xanthomas, and/or arcus corneae, and early CVD. Lipid measurements were repeated to ascertain the existence of primary isolated hypercholesterolemia due to elevated LDL. Family history and pedigrees were investigated. Informed consent was obtained for all subjects included in this study. Family HC2 has been previously reported and described at length (Varret et al, 1999). Functional tests showed normal binding, internalization and degradation of LDL particles in fibroblasts from the probands (HC2-II-9) (Hobbs et al, 1989). Five other families (HC35, HC60, HC92, HC122, HC243) were studied representing 26 affected and 26 unaffected subjects. For affected subjects, mean total and LDL cholesterol were 3.27 g/L±0.77 and 2.47±0.76 g/L, respectively.

DNA Analysis and Genotyping

DNA was isolated from whole blood samples as previously described (Collod et al, 1994). All families were tested with polymorphic markers of the LDLR and APOB genes. For the LDLR, two intragenic markers (D19S584 in intron 1 and the (TA)$_n$ in exon 18) and two flanking markers (D19S394 and D19S221) were studied. The 5'HVR (TG repeat) and 3'HVR (VNTR) were studied for the APOB gene and screening for the R3500Q mutation as reported (Rabès et al, 1997). Genotyping at 1p34-p32 was performed using 11 microsatellites from the Genethon map (D1S472, D1S2722, D1S211, D1S197, D1S231, D1S2661; D1S417, D1S475, D1S200, D1S2742, D1S2890) as reported (Collod et al, 1994).

Linkage Analysis

Parametric linkage analyses were performed with accepted parameters of ADH: dominant transmission of the trait, penetrance of 0.9 for heterozygotes, and a frequency of the disease allele of 1/500. The MLINK and LINKMAP programs (Ott, 1991), and the VITESSE program (O'Connell & Weeks, 1995) were used to perform the two-point and multipoint LOD score analyses. Microsatellite allele frequencies were calculated among the unrelated family members. Linkage was investigated with the assumption of equal female-to-male recombination rates.

Candidate Gene Identification and Analysis

Microsatellites of the 1p34-p32 region were localized on sequences of the Human Genome Project, a physical map of the region was in agreement with the one published by UCSC: URL genome.ucsc.edu. Repeat Masker and Genscan programs allowed the prediction and the identification in the Genbank database of positional candidate genes. The Blast program (URL ncbi.nlm.nih.gov/BLAST/) was used to localize precisely the candidate genes. The intron/exon structure of the 8 functional candidates was determined and primers designed with the Mac Vector® software. 137 primer pairs were chosen at approximatively 100 bp surrounding each exon boundary. PCRs were performed with thermostable DNA polymerase from LAROVA Biochemic GmbH (Germany) on GeneAmp® PCR system 9600 (Perkin Elmer). Fluorescent sequencing was carried-out with Big Dye Terminator version 1.0 on GeneAmp® PCR system 9700 (Perkin Elmer) apparatus, under conditions supplied by the manufacturer. Electrophoregrams were analyzed using Sequencing Analysis® 3.4 and SeqED®.

PCSK9 Analysis

Primers designed to study the 12 exons of NARC-1, and their conditions of amplification are available on request. Major rearrangements for NARC-1 were investigated by Southern blot as reported (Collot et al, 1994). A rapid detection method of the S127R mutation using PCR amplification followed by digestion by MnlI was developed. After amplification of exon 2, the 543 bp PCR product was digested by 5 U MnlI enzyme. After electrophoresis on a 2% agarose gel, fragments of 208, 203 and 60 bp were distinguished in the normal allele, while fragments of 208, 143 and 60 bp appeared in the mutated alleles (the 203 bp normal fragment was divided in fragments of 143 and 60 bp and the two 60 bp fragments generated comigrated). Segregation analysis of this mutation in families HC2 and HC92 and analysis of 200 chromosomes from unaffected persons of French descent were tested both by sequencing and by the MnlI-digestion.

NARC-1 Mutants and Protein Studies

HEK293 cells were transiently transfected with pIRES2 recombinant vectors (Seidah et al, 2003) expressing wild type hNARC-1-V5 (WT) or its mutants H226A, F216L, S127R, S127A, S127P and 15_16insL (+L). 24 h later the cells were pulse-labeled with [$^{35}$S] EasyTag Express mix for 4 h. Cell extracts and media were immunoprecipitated with a V5 antibody and the precipitates resolved by SDS-PAGE on an 8% Glycine gels.

Accession Numbers for the Genes Tested

EPS15, NM_001981; OSBPL9, NM_024586; SCP2, NM_002979; LRP8, NM_004631; DHCR24, NM_014762; PRKAA2, NM_006252; DAB$_1$, NM_021080); NARC-1: human AX207686 (gi:15422368); *Mus musculus*: AX207688; *Rattus norvegicus* AX207690.

REFERENCES

Austin, M A., King, M C., Bawol, R D., Hulley, S B. & Friedman, G D. *Am. J. Epidemiol.* 125, 308-318 (1987).
Barrett, H. R. et al. *Metabolism* 47, 484-492 (1998).
Beghin L. et al. *J. Lipid Res.* 41, 1172-1176 (2000).
Bostrom, K. & al *J. Biol. Chem.* 263, 4434-4442 (1988).
Brown, M S. & Goldstein, J L. *Proc. Natl. Acad. Sci. USA.* 96, 11041-11048 (1999).
Burnett, J. R. et al. *Arterioscler. Thromb. Vasc. Biol.* 17, 2589-2600 (1997).
Cavallo, D., Rudy, D., Mohammadi, A., Macri, J. & Adeli K. *J. Biol. Chem.* 274, 23135-23143 (1999).
Cobelli, C., Toffolo, G. & Fodter, D. M. *Am. J. Physiol.* 262, E968-E975 (1992).
Collod, G. et al. *Nature Genet.* 8, 264-268 (1994).
Desnick, R. J.; Ostasiewicz, L. T.; Tishler, P. A.; Mustajoki, P. *J. Clin. Invest.* 76, 865-874, (1985).
Egusa, D., Brady, W., Grundy, S. M & Howard, B. V. *J. Lipid Res.* 24, 1261-1267 (1983).
Elagoz, A., Benjannet, S., Mammarbassi, A., Wickham, L. & Seidah N G. *J. Biol. Chem.* 277, 11265-11275 (2002).
Felsher, B. F., Carpio, N. M.; Engleking, D. W.& Nunn, A. T. *N. Eng. J. Med.* 306, 766-769 (1982).
Fredrickson, D S., Levy, R I. & Lees, R S. *N. Eng.l J Med.* 276, 273-281 (1967):
Frenais, R. et al. *Diabetologia.* 40, 578-583 (1997).
Ginsberg, H. N., Le, N. A. & Gibson J. C. *J. Clin. Invest.* 75, 614-623 (1985).
Goldstein, J L., Schrott, H G., Hazzard, W R., Bierman, E L. & Motulsky A G. *J. Clin. Invest.* 52, 1544-1568 (1973).
Goldstein, J L. & Brown, M S., *Johns Hopkins Med. J* 143, 8-16 (1978).
Hobbs, H H., et al. *J. Clin. Invest.* 84, 656-664 (1989).
Hunt, S C. et al. *Arterioscler. Thromb. Vasc. Biol.* 20, 1089-1093 (2000).
Innerarity, T L. et al. *Proc. Natl. Acad. Sci. USA.* 84, 6919-6923 (1987).
Jackson, R. S. & al. *Nature Genet.* 16, 303-306 (1997).
Khachadurian, A K., *Am. J. Med.* 37, 402-407, (1964).
Lusis, A J. Atherosclerosis. *Nature.* 407, 233-241 (2000).
Maugeais, C., Ouguerram, K., Mahot, P., Krempf, M. & Magot, T., *Diabetes Metab.* 22, 57-63 (1996).
Maugeais, C., Ouguerram, K., Krernpf, M. & Magot, T. *Clin. Chem. Lab. Med.* 36, 739-745 (1998).
Morganroth, J., Levy, R I., McMahon, A E. & Gotto, A M Jr. *J. Pediatr.* 85, 639-643 (1974).
O'Connell, J R. & Weeks D E. *Nature Genet.* 11, 402-408 (1995)
Ott, J. Analysis of human genetic linkage, revised ed. The Johns Hopkins University Press, Baltimore and London (1991)
Perusse, L. *Arteriosclerosis.* 9, 308-318 (1989).
Pont, F., Duvillard, L., Verges, B. & Gambert, P. *Arterioscier. Thromb. Vasc. Biol.* 18, 853-860 (1998).
Rabès, J P. et al. *Hum. Mutat.* 10: 160-163 (1997).
Rice, T., Vogler, G P., Laskarzewski, P M., Perry, T S. & Rao, D C. *Hum. Biol.* 63, 419-439 (1991).
Ruoslahti, E. *Annu. Rev. Cell. Dev. Biol.* 12, 697-715 (1996).
Saint-Jore, B. et al. *Eur. J. Hum. Genet.* 8, 621-630 (2000).
Sass, C., Giroux, L M., Lussier-Cacan, S., Davignon, J. & Minnich, A. *J. Biol. Chem.* 270, 25166-71 (1995).
Seidah, N G. et al. *Proc. Natl. Acad. Sci. USA.* 100, 928-933 (2003).
Senaphthy, P., Shapiro, M B. & Harris, N L. *Methods Enzymol.* 183, 252-278 (1990).
Shapiro, M B. & Senaphthy, P. *Nucleic Acids Res.* 15, 7155-7174 (1987).
Steinmetz, J., Cholestérol total. In: Siest G, Henny J, Schiele F (eds). Références en biologie clinique. Elsevier, 1990. Paris, pp 190-209.
Varret, M. et al. *Am. J. Hum. Genet.* 64, 1378-1387 (1999).

TABLE 1

Regional lod scores obtained in the HC92 family

| Locus | Distance[1] | LOD score at θ | | | | | | | | $Z_{max}$ | $θ_{max}$ |
|---|---|---|---|---|---|---|---|---|---|---|---|
| | | 0.00 | 0.001 | 0.01 | 0.05 | 0.10 | 0.20 | 0.30 | 0.40 | | |
| D1S2722 | ... | 2.17 | 2.17 | 2.13 | 1.96 | 1.75 | 1.31 | 0.87 | 0.44 | 2.17 | 0.00 |
| D1S211 | 0.025 | −0.77 | 1.53 | 2.46 | 2.86 | 2.77 | 2.22 | 1.48 | 0.67 | 2.86 | 0.05 |

TABLE 1-continued

Regional lod scores obtained in the HC92 family

| Locus | Distance[1] | LOD score at θ | | | | | | | | $Z_{max}$ | $θ_{max}$ |
|---|---|---|---|---|---|---|---|---|---|---|---|
| | | 0.00 | 0.001 | 0.01 | 0.05 | 0.10 | 0.20 | 0.30 | 0.40 | | |
| D1S197 | 0.063 | −1.73 | −1.72 | −1.62 | −1.20 | −0.86 | −0.48 | −0.26 | −0.11 | −0.11 | 0.40 |
| D1S231 | 0.014 | 1.08 | 1.08 | 1.08 | 1.06 | 1.00 | 0.81 | 0.57 | 0.30 | 1.08 | 0.00 |
| D1S417 | 0.036 | 3.12 | 3.11 | 3.08 | 2.89 | 2.61 | 1.93 | 1.16 | 0.43 | 3.12 | 0.00 |
| D1S200 | 0.007 | 2.50 | 2.49 | 2.45 | 2.25 | 1.98 | 1.44 | 0.87 | 0.33 | 2.50 | 0.00 |
| D1S2742 | 0.007 | 4.26 | 4.26 | 4.21 | 3.97 | 3.61 | 2.76 | 1.79 | 0.77 | 4.26 | 0.00 |
| D1S2890 | 0.013 | 0.84 | 1.29 | 2.08 | 2.54 | 2.52 | 2.05 | 1.35 | 0.58 | 2.54 | 0.05 |

[1]Distance between two adjacent markers in θ

TABLE 2

Polymorphisms identified in the PCSK9 gene

| Exon | Polymorp. Name | Nucleotidic Variation | Position SEQ ID N°3 | Amino acid variation | Nb of indiv. tested | Frequency |
|---|---|---|---|---|---|---|
| 1 | A | C→T | 916 | 5′ UTR | 113 | 0.119 |
| | B | Leu stretch insCTG | 1022-1042 | 15_16insL (+L) | 113 | 0.168 |
| | C | G→T | 1116 | R46L | 113 | 0.022 |
| | D | C→T | 1120 | S47S | 113 | 0.016 |
| | E | C→T | 1137 | A53V | 113 | 0.124 |
| 2 | F | T→C | 4824 | Intronic | 100 | 0.040 |
| 3 | G | G→A | 7464 | Intronic | 25 | 0.016 |
| 4 | H | G→C | 13327 | Intronic | 100 | 0.548 |
| | I | G→C | 13349 | Intronic | 100 | 0.547 |
| | J | G→A | 13406 | Intronic | 100 | 0.063 |
| | K | G→A | 13559 | Intronic | 100 | 0.052 |
| | L | C→A | 13626 | Intronic | 100 | 0.076 |
| | M | A→G | 13632 | Intronic | 100 | 0.382 |
| 5 | N | G→A | 13753 | Intronic | 23 | 0.020 |
| | O | C→T | 13781 | Intronic | 23 | 0.280 |
| | P | A→G | 13932 | Intronic | 23 | 0.240 |
| | Q | A→C | 13993 | Intronic | 23 | 0.170 |
| 8 | R | T→C | 19444 | Intronic | 20 | 0.175 |
| 9 | S | T→C | 19576 | Intronic | 113 | 0.137 |
| | T | G→A | 19657 | V460V | 113 | 0.128 |
| | U | A→G | 19697 | I474V | 113 | 0.141 |
| 10 | V | C→T | 20845 | Intronic | 24 | 0.040 |
| | W | A→G | 20846 | Intronic | 24 | 0.146 |
| 11 | X | A→G | 22769 | Intronic | 20 | 0.030 |
| 12 | Y | A→G | 24633 | E670G | 79 | 0.082 |

Marker haplotypes surrounding the mutations of PCSK9: markers are given in physical order from telomere (left) to centromere (right). A common disease haplotype segregates with the S127R mutation in both the HC92 and the HC2 family.

TABLE 4

Mutations identified in the PCSK9 gene

| Exon | Nucleotidic Variation | Position SEQ ID N°1 | Amino acid variation | Effect |
|---|---|---|---|---|
| 1 | +CTA | 314-316 | Insert L23 | |
| 1 | +CTACTA | 314-319 | Insert LL23, 24 | |
| 1 | CAG→GAG | 335-337 | Q31N | |
| 1 | TGC→GCA | 443-445 | C67A | |
| 2 | ACC→GCC | 473-475 | T77A | |
| 2 | TAC→GCC | 476-478 | Y78A | Inactive zymogen |
| 2 | GTG→GCG | 479-481 | V79A | |
| 2 | GTG→GCG | 482-484 | V80A | Inactive zymogen |
| 2 | GTG→ATT | 482-484 | V80I | |
| 2 | GTG→GCG | 482-484 | V80A | |
| 2 | GTG→TTG | 482-484 | V80L | Inactive zymogen |
| 2 | GTG→GCG | 485-487 | V81A | |
| 2 | CTG→GCG | 488-490 | L82A | Inactive zymogen |
| 2 | CTG→GTG | 488-490 | L82V | Partially active enzyme |
| 2 | CTG→CCG | 488-490 | L82P | Inactive zymogen |
| 2 | GTGGTGGTG→CGGCGGCTG | 485-490 | V79R & V80R & V81L | Inactive zymogen |
| 2 | GTG→ATT & AAG→ATG | 479-481 & 491-493 | V79I & K83M | Increased zymogen activation |

TABLE 3

Haplotypes of affected subjects from the three ADH families

| | | Markers in 1p32 region | | | | | | |
|---|---|---|---|---|---|---|---|---|
| | | | PCSK9 | | | | | |
| | | | Exon 1 | Exon 4 | | Exon 9 | | |
| Family | Mutation | D1S417 | Polym. B | Polym. H | Polym. I | Polym. M | Polym. U | D1S200 | D1S2742 |
| HC92 | S127R | 2 | No | G | G | A | A | 3 | 6 |
| HC2 | S127R | 2 | No | G | G | A | A | 3 | 6 |
| HC60 | F216L | 4 | No | C | C | G | G | — | 3 |

TABLE 4-continued

Mutations identified in the PCSK9 gene

| Exon | Nucleotidic Variation | Position SEQ ID N°1 | Amino acid variation | Effect |
|---|---|---|---|---|
| 2 | GAG→GCG | 494-496 | E84A | None |
| 2 | GAG→GCG | 497-499 | E85A | |
| 2 | ACC→GCC | 500-502 | T86A | |
| 2 | CAC→GCC | 503-505 | H87A | |
| 2 | CTC→GCC | 506-508 | L88A | |
| 2 | GCTGCC→CGTAGA | 548-553 | A102R & A103R | Inactive zymogen |
| 2 | ACC→ATC | 569-571 | T109I | Increased zymogen activation |
| 2 | GTG→ATT & AAG→ATG & CTG→CCG | 479-481 & 491-493 & 578-580 | V79I & K83M & L112P | Inactive zymogen |
| 2 | ATG→GCG | 620-622 | M126A | Decreased zymogen activation |
| 2 | AGT→CGT | 623-625 | S127R | Decreased zymogen activation |
| 2 | AGT→GCT | 623-625 | S127A | Decreased zymogen activation |
| 2 | AGT→CCT | 623-625 | S127P | None |
| 3 | CCC→TAC | 656-658 | P138Y | Decreased zymogen activation |
| 3 | ATC→CCC | 671-673 | I143P | Inactive zymogen |
| 4 | TTC→CTC | 890-892 | F216L | |
| 4 | AGA→AGT | 896-898 | R218S | |
| 5 | CAT→GCT | 920-922 | H226A | Inactive zymogen |
| 5 | CGG→TGG | 953-955 | R237W | |
| 6 | AAC→GCA | 1193-1195 | N317A | Inactive zymogen |
| 10 | AAC→GCG/GCA/GCC/GCT | 1841-1843 | N533A | |
| 10 | AAC→CAG | 1841-1843 | N533Q | Loss of N-glycosylation |
| 11 | AAC→CAG | 2000-2002 | N586Q | |
| 12 | AAC→CAG | 2198-2200 | N652Q | |

---

What is claimed is:

1. A method of detecting the presence of or predisposition to autosomal dominant hypercholesterolemia in a human subject, the method comprising (i) providing a nucleic acid sample comprising a PCSK9 nucleic acid sequence from the subject and (ii) detecting the presence of an alteration in the PCSK9 nucleic acid sequence, the alteration being a T→A or T→G substitution at nucleotide 625 of SEQ ID NO:1, said alteration in said nucleic acid sequence being indicative of the presence of or predisposition to autosomal dominant hypercholesterolemia.

2. The method according to claim 1, wherein said alteration leads to a decrease in expression of the N2 form of NARC-1 encoded by the PCSK9 nucleic acid sequence.

3. The method according to claim 1, wherein said alteration is a T→A substitution at nucleotide 625 of SEQ ID NO: 1.

4. The method according to claim 2, wherein said alteration in the nucleic acid is one which encodes for an amino acid substitution of a Serine at position 127.

5. The method according to claim 2, wherein said alteration in the nucleic acid is one which encodes for an amino acid substitution of a Serine at position 127 by an Arginine.

* * * * *

SEQUENCE LISTING

```
<160> NUMBER OF SEQ ID NOS: 3

<210> SEQ ID NO 1
<211> LENGTH: 3617
<212> TYPE: DNA
<213> ORGANISM: Homo sapiens
<220> FEATURE:
<221> NAME/KEY: CDS
<222> LOCATION: (245)..(2320)
<223> OTHER INFORMATION:
<220> FEATURE:
<221> NAME/KEY: mutation
<222> LOCATION: (625)..(625)
<223> OTHER INFORMATION: T->A
<220> FEATURE:
<221> NAME/KEY: mutation
<222> LOCATION: (890)..(890)
<223> OTHER INFORMATION: T->C

<400> SEQUENCE: 1
cccacgcgtc cggcctggag gagtgagcca ggcagtgaga ctggctcggg cgggccggga      60
cgcgtcgttg cagcagcggc tcccagctcc cagccaggat tccgcgcgcc ccttcacgcg     120
ccctgctcct gaacttcagc tcctgcacag tcctccccac cgcaaggctc aaggcgccgc     180
cggcgtggac cgcgcacggc ctctaggtct cctcgccagg acagcaacct ctcccctggc     240 cctc atg ggc acc gtc agc tcc agg cgg tcc tgg tgg ccg ctg cca ctg      289
     Met Gly Thr Val Ser Ser Arg Arg Ser Trp Trp Pro Leu Pro Leu
     1               5                  10                  15 ctg ctg ctg ctg ctg ctg ctc ctg ggt ccc gcg ggc gcc cgt gcg cag      337
Leu Leu Leu Leu Leu Leu Leu Leu Gly Pro Ala Gly Ala Arg Ala Gln
                20                  25                  30 gag gac gag gac ggc gac tac gag gag ctg gtg cta gcc ttg cgt tcc      385
Glu Asp Glu Asp Gly Asp Tyr Glu Glu Leu Val Leu Ala Leu Arg Ser
```

|   |   |
|---|---|
| gag gag gac ggc ctg gcc gaa gca ccc gag cac gga acc aca gcc acc<br>Glu Glu Asp Gly Leu Ala Glu Ala Pro Glu His Gly Thr Thr Ala Thr<br>           50                    55                    60 | 433 |
| ttc cac cgc tgc gcc aag gat ccg tgg agg ttg cct ggc acc tac gtg<br>Phe His Arg Cys Ala Lys Asp Pro Trp Arg Leu Pro Gly Thr Tyr Val<br> 65                    70                    75 | 481 |
| gtg gtg ctg aag gag gag acc cac ctc tcg cag tca gag cgc act gcc<br>Val Val Leu Lys Glu Glu Thr His Leu Ser Gln Ser Glu Arg Thr Ala<br> 80                    85                    90                    95 | 529 |
| cgc cgc ctg cag gcc cag gct gcc cgc cgg gga tac ctc acc aag atc<br>Arg Arg Leu Gln Ala Gln Ala Ala Arg Arg Gly Tyr Leu Thr Lys Ile<br>           100                    105                   110 | 577 |
| ctg cat gtc ttc cat ggc ctt ctt cct ggc ttc ctg gtg aag atg agt<br>Leu His Val Phe His Gly Leu Leu Pro Gly Phe Leu Val Lys Met Ser<br>         115                     120                    125 | 625 |
| ggc gac ctg ctg gag ctg gcc ttg aag ttg ccc cat gtc gac tac atc<br>Gly Asp Leu Leu Glu Leu Ala Leu Lys Leu Pro His Val Asp Tyr Ile<br>      130                     135                    140 | 673 |
| gag gag gac tcc tct gtc ttt gcc cag agc atc ccg tgg aac ctg gag<br>Glu Glu Asp Ser Ser Val Phe Ala Gln Ser Ile Pro Trp Asn Leu Glu<br>     145                    150                    155 | 721 |
| cgg att acc cct cca cgg tac cgg gcg gat gaa tac cag ccc ccc gac<br>Arg Ile Thr Pro Pro Arg Tyr Arg Ala Asp Glu Tyr Gln Pro Pro Asp<br>160                    165                    170                    175 | 769 |
| gga ggc agc ctg gtg gag gtg tat ctc cta gac acc agc ata cag agt<br>Gly Gly Ser Leu Val Glu Val Tyr Leu Leu Asp Thr Ser Ile Gln Ser<br>           180                    185                   190 | 817 |
| gac cac cgg gaa atc gag ggc agg gtc atg gtc acc gac ttc gag aat<br>Asp His Arg Glu Ile Glu Gly Arg Val Met Val Thr Asp Phe Glu Asn<br>         195                    200                    205 | 865 |
| gtg ccc gag gag gac ggg acc cgc ttc cac aga cag gcc agc aag tgt<br>Val Pro Glu Glu Asp Gly Thr Arg Phe His Arg Gln Ala Ser Lys Cys<br>      210                     215                    220 | 913 |
| gac agt cat ggc acc cac ctg gca ggg gtg gtc agc ggc cgg gat gcc<br>Asp Ser His Gly Thr His Leu Ala Gly Val Val Ser Gly Arg Asp Ala<br>225                    230                    235 | 961 |
| ggc gtg gcc aag ggt gcc agc atg cgc agc ctg cgc gtg ctc aac tgc<br>Gly Val Ala Lys Gly Ala Ser Met Arg Ser Leu Arg Val Leu Asn Cys<br>240                    245                    250                    255 | 1009 |
| caa ggg aag ggc acg gtt agc ggc acc ctc ata ggc ctg gag ttt att<br>Gln Gly Lys Gly Thr Val Ser Gly Thr Leu Ile Gly Leu Glu Phe Ile<br>           260                    265                   270 | 1057 |
| cgg aaa agc cag ctg gtc cag cct gtg ggg cca ctg gtg gtg ctg ctg<br>Arg Lys Ser Gln Leu Val Gln Pro Val Gly Pro Leu Val Val Leu Leu<br>         275                    280                   285 | 1105 |
| ccc ctg gcg ggt ggg tac agc cgc gtc ctc aac gcc gcc tgc cag cgc<br>Pro Leu Ala Gly Gly Tyr Ser Arg Val Leu Asn Ala Ala Cys Gln Arg<br>      290                     295                    300 | 1153 |
| ctg gcg agg gct ggg gtc gtg ctg gtc acc gct gcc ggc aac ttc cgg<br>Leu Ala Arg Ala Gly Val Val Leu Val Thr Ala Ala Gly Asn Phe Arg<br>305                    310                    315 | 1201 |
| gac gat gcc tgc ctc tac tcc cca gcc tca gct ccc gag gtc atc aca<br>Asp Asp Ala Cys Leu Tyr Ser Pro Ala Ser Ala Pro Glu Val Ile Thr<br>320                    325                    330                    335 | 1249 |
| gtt ggg gcc acc aat gcc cag gac cag ccg gtg acc ctg ggg act ttg<br>Val Gly Ala Thr Asn Ala Gln Asp Gln Pro Val Thr Leu Gly Thr Leu<br>           340                    345                   350 | 1297 |
| ggg acc aac ttt ggc cgc tgt gtg gac ctc ttt gcc cca ggg gag gac | 1345 |

```
                                            -continued

Gly Thr Asn Phe Gly Arg Cys Val Asp Leu Phe Ala Pro Gly Glu Asp
            355                 360                 365 atc att ggt gcc tcc agc gac tgc agc acc tgc ttt gtg tca cag agt     1393
Ile Ile Gly Ala Ser Ser Asp Cys Ser Thr Cys Phe Val Ser Gln Ser
            370                 375                 380 ggg aca tca cag gct gct gcc cac gtg gct ggc att gca gcc atg atg     1441
Gly Thr Ser Gln Ala Ala Ala His Val Ala Gly Ile Ala Ala Met Met
385                 390                 395 ctg tct gcc gag ccg gag ctc acc ctg gcc gag ttg agg cag aga ctg     1489
Leu Ser Ala Glu Pro Glu Leu Thr Leu Ala Glu Leu Arg Gln Arg Leu
400                 405                 410                 415 atc cac ttc tct gcc aaa gat gtc atc aat gag gcc tgg ttc cct gag     1537
Ile His Phe Ser Ala Lys Asp Val Ile Asn Glu Ala Trp Phe Pro Glu
            420                 425                 430 gac cag cgg gta ctg acc ccc aac ctg gtg gcc gcc ctg ccc ccc agc     1585
Asp Gln Arg Val Leu Thr Pro Asn Leu Val Ala Ala Leu Pro Pro Ser
            435                 440                 445 acc cat ggg gca ggt tgg cag ctg ttt tgc agg act gtg tgg tca gca     1633
Thr His Gly Ala Gly Trp Gln Leu Phe Cys Arg Thr Val Trp Ser Ala
            450                 455                 460 cac tcg ggg cct aca cgg atg gcc aca gcc atc gcc cgc tgc gcc cca     1681
His Ser Gly Pro Thr Arg Met Ala Thr Ala Ile Ala Arg Cys Ala Pro
465                 470                 475 gat gag gag ctg ctg agc tgc tcc agt ttc tcc agg agt ggg aag cgg     1729
Asp Glu Glu Leu Leu Ser Cys Ser Ser Phe Ser Arg Ser Gly Lys Arg
480                 485                 490                 495 cgg ggc gag cgc atg gag gcc caa ggg ggc aag ctg gtc tgc cgg gcc     1777
Arg Gly Glu Arg Met Glu Ala Gln Gly Gly Lys Leu Val Cys Arg Ala
                500                 505                 510 cac aac gct ttt ggg ggt gag ggt gtc tac gcc att gcc agg tgc tgc     1825
His Asn Ala Phe Gly Gly Glu Gly Val Tyr Ala Ile Ala Arg Cys Cys
            515                 520                 525 ctg cta ccc cag gcc aac tgc agc gtc cac aca gct cca cca gct gag     1873
Leu Leu Pro Gln Ala Asn Cys Ser Val His Thr Ala Pro Pro Ala Glu
            530                 535                 540 gcc agc atg ggg acc cgt gtc cac tgc cac caa cag ggc cac gtc ctc     1921
Ala Ser Met Gly Thr Arg Val His Cys His Gln Gln Gly His Val Leu
545                 550                 555 aca ggc tgc agc tcc cac tgg gag gtg gag gac ctt ggc acc cac aag     1969
Thr Gly Cys Ser Ser His Trp Glu Val Glu Asp Leu Gly Thr His Lys
560                 565                 570                 575 ccg cct gtg ctg agg cca cga ggt cag ccc aac cag tgc gtg ggc cac     2017
Pro Pro Val Leu Arg Pro Arg Gly Gln Pro Asn Gln Cys Val Gly His
                580                 585                 590 agg gag gcc agc atc cac gct tcc tgc tgc cat gcc cca ggt ctg gaa     2065
Arg Glu Ala Ser Ile His Ala Ser Cys Cys His Ala Pro Gly Leu Glu
            595                 600                 605 tgc aaa gtc aag gag cat gga atc ccg gcc cct cag gag cag gtg acc     2113
Cys Lys Val Lys Glu His Gly Ile Pro Ala Pro Gln Glu Gln Val Thr
            610                 615                 620 gtg gcc tgc gag gag ggc tgg acc ctg act ggc tgc agt gcc ctc cct     2161
Val Ala Cys Glu Glu Gly Trp Thr Leu Thr Gly Cys Ser Ala Leu Pro
625                 630                 635 ggg acc tcc cac gtc ctg ggg gcc tac gcc gta gac aac acg tgt gta     2209
Gly Thr Ser His Val Leu Gly Ala Tyr Ala Val Asp Asn Thr Cys Val
640                 645                 650                 655 gtc agg agc cgg gac gtc agc act aca ggc agc acc agc gaa gag gcc     2257
Val Arg Ser Arg Asp Val Ser Thr Thr Gly Ser Thr Ser Glu Glu Ala
                660                 665                 670
```

```
gtg aca gcc gtt gcc atc tgc tgc cgg agc cgg cac ctg gcg cag gcc    2305
Val Thr Ala Val Ala Ile Cys Cys Arg Ser Arg His Leu Ala Gln Ala
            675                 680                 685 tcc cag gag ctc cag tgacagcccc atcccaggat gggtgtctgg ggagggtcaa    2360
Ser Gln Glu Leu Gln
        690 gggctggggc tgagctttaa aatggttccg acttgtccct ctctcagccc tccatggcct   2420 ggcacgaggg gatggggatg cttccgcctt tccggggctg ctggcctggc ccttgagtgg   2480 ggcagcctcc ttgcctggaa ctcactcact ctgggtgcct cctccccagg tggaggtgcc   2540 aggaagctcc ctccctcact gtggggcatt tcaccattca aacaggtcga gctgtgctcg   2600 ggtgctgcca gctgctccca atgtgccgat gtccgtgggc agaatgactt ttattgagct   2660 cttgttccgt gccaggcatt caatcctcag gtctccacca aggaggcagg attcttccca   2720 tgatagggg aggggcggt agggctgca gggacaaaca tcgttggggg gtgagtgtga     2780 aagtgctga tggccctcat ctccagctaa ctgtggagaa gccctgggg gctccctgat    2840 taatggaggc ttagctttct ggatggcatc tagccagagg ctggagacag gtgtgcccct   2900 ggtggtcaca ggctgtgcct tggtttcctg agccaccttt actctgctct atgccaggct   2960 gtgctagcaa cacccaaagg tggcctgcgg ggagccatca cctaggactg actcggcagt   3020 gtgcagtggt gcatgcactg tctcagccaa cccgctccac tacccggcag ggtacacatt   3080 cgcaccccta cttcacagag gaagaaacct ggaaccagag ggggcgtgcc tgccaagctc   3140 acacagcagg aactgagcca gaaacgcaga ttgggctggc tctgaagcca agcctcttct   3200 tacttcaccc ggctgggctc ctcatttta cgggtaacag tgaggctggg aaggggaaca    3260 cagaccagga agctcggtga gtgatggcag aacgatgcct gcaggcatgg aacttttttcc  3320 gttatcaccc aggcctgatt cactggcctg gcggagatgc ttctaaggca tggtcggggg   3380 agagggccaa caactgtccc tccttgagca ccagccccac ccaagcaagc agacatttat   3440 cttttgggtc tgtcctctct gttgcctttt tacagccaac ttttctagac ctgttttgct   3500 tttgtaactt gaagatattt attctggggtt ttgtagcatt tttattaata tggtgacttt   3560 ttaaaataaa aacaaacaaa cgttgtccta aaaaaaaaaa aaaaawaaa aaaaaa       3617

<210> SEQ ID NO 2
<211> LENGTH: 692
<212> TYPE: PRT
<213> ORGANISM: Homo sapiens
<220> FEATURE:
<221> NAME/KEY: ACT_SITE
<222> LOCATION: (186)..(186)
<223> OTHER INFORMATION: Asp
<220> FEATURE:
<221> NAME/KEY: ACT_SITE
<222> LOCATION: (226)..(226)
<223> OTHER INFORMATION: His
<220> FEATURE:
<221> NAME/KEY: ACT_SITE
<222> LOCATION: (317)..(317)
<223> OTHER INFORMATION: Asn
<220> FEATURE:
<221> NAME/KEY: ACT_SITE
<222> LOCATION: (386)..(386)
<223> OTHER INFORMATION: Ser
<220> FEATURE:
<221> NAME/KEY: ACT_SITE
<222> LOCATION: (186)..(186)
<223> OTHER INFORMATION: Asp
<220> FEATURE:
<221> NAME/KEY: SITE
<222> LOCATION: (127)..(127)
<223> OTHER INFORMATION: Xaa is Ser or Arg ; Substitution Ser -> Arg
```

```
<220> FEATURE:
<221> NAME/KEY: SITE
<222> LOCATION: (216)..(216)
<223> OTHER INFORMATION: Xaa is Phe or Leu ; Substitution Phe -> Leu
<220> FEATURE:
<221> NAME/KEY: VARIANT
<222> LOCATION: (46)..(46)
<223> OTHER INFORMATION: Xaa is Arg or Leu ; Substitution Arg -> Leu
<220> FEATURE:
<221> NAME/KEY: VARIANT
<222> LOCATION: (53)..(53)
<223> OTHER INFORMATION: Xaa is Ala or Val ; Substitution Ala -> Val
<220> FEATURE:
<221> NAME/KEY: VARIANT
<222> LOCATION: (474)..(474)
<223> OTHER INFORMATION: Xaa is Ile or Val ; Substitution Ile -> Val
<220> FEATURE:
<221> NAME/KEY: VARIANT
<222> LOCATION: (670)..(670)
<223> OTHER INFORMATION: Xaa is Glu or Gly ; Substition Glu -> Gly

<400> SEQUENCE: 2

Met Gly Thr Val Ser Ser Arg Arg Ser Trp Trp Pro Leu Pro Leu Leu
 1               5                  10                  15

Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Xaa Ser Glu
        35                  40                  45

Glu Asp Gly Leu Xaa Glu Ala Pro Glu His Gly Thr Thr Ala Thr Phe
    50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Xaa Gly
        115                 120                 125

Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
        195                 200                 205

Pro Glu Glu Asp Gly Thr Arg Xaa His Arg Gln Ala Ser Lys Cys Asp
    210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
        275                 280                 285

Leu Ala Gly Gly Tyr Ser Arg Val Leu Asn Ala Ala Cys Gln Arg Leu
    290                 295                 300
```

```
Ala Arg Ala Gly Val Val Leu Val Thr Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
                340                 345                 350

Thr Asn Phe Gly Arg Cys Val Asp Leu Phe Ala Pro Gly Glu Asp Ile
            355                 360                 365

Ile Gly Ala Ser Ser Asp Cys Ser Thr Cys Phe Val Ser Gln Ser Gly
370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
                420                 425                 430

Gln Arg Val Leu Thr Pro Asn Leu Val Ala Ala Leu Pro Pro Ser Thr
            435                 440                 445

His Gly Ala Gly Trp Gln Leu Phe Cys Arg Thr Val Trp Ser Ala His
450                 455                 460

Ser Gly Pro Thr Arg Met Ala Thr Ala Xaa Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
                500                 505                 510

Asn Ala Phe Gly Gly Glu Gly Val Tyr Ala Ile Ala Arg Cys Cys Leu
            515                 520                 525

Leu Pro Gln Ala Asn Cys Ser Val His Thr Ala Pro Pro Ala Glu Ala
530                 535                 540

Ser Met Gly Thr Arg Val His Cys His Gln Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590

Glu Ala Ser Ile His Ala Ser Cys Cys His Ala Pro Gly Leu Glu Cys
                595                 600                 605

Lys Val Lys Glu His Gly Ile Pro Ala Pro Gln Glu Gln Val Thr Val
610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Xaa Ala Val
            660                 665                 670

Thr Ala Val Ala Ile Cys Cys Arg Ser Arg His Leu Ala Gln Ala Ser
            675                 680                 685

Gln Glu Leu Gln
    690

<210> SEQ ID NO 3
<211> LENGTH: 26220
```

```
<212> TYPE: DNA
<213> ORGANISM: Homo sapiens
<220> FEATURE:
<221> NAME/KEY: exon
<222> LOCATION: (980)..(1186)
<223> OTHER INFORMATION: exon 1
<220> FEATURE:
<221> NAME/KEY: exon
<222> LOCATION: (4985)..(5176)
<223> OTHER INFORMATION: exon 2
<220> FEATURE:
<221> NAME/KEY: exon
<222> LOCATION: (7665)..(7788)
<223> OTHER INFORMATION: exon 3
<220> FEATURE:
<221> NAME/KEY: exon
<222> LOCATION: (13417)..(13550)
<223> OTHER INFORMATION: exon 4
<220> FEATURE:
<221> NAME/KEY: exon
<222> LOCATION: (13788)..(13929)
<223> OTHER INFORMATION: exon 5
<220> FEATURE:
<221> NAME/KEY: exon
<222> LOCATION: (17130)..(17326)
<223> OTHER INFORMATION: exon 6
<220> FEATURE:
<221> NAME/KEY: exon
<222> LOCATION: (18464)..(18647)
<223> OTHER INFORMATION: exon 7
<220> FEATURE:
<221> NAME/KEY: exon
<222> LOCATION: (19169)..(19342)
<223> OTHER INFORMATION: exon 8
<220> FEATURE:
<221> NAME/KEY: exon
<222> LOCATION: (19632)..(19780)
<223> OTHER INFORMATION: exon 9
<220> FEATURE:
<221> NAME/KEY: exon
<222> LOCATION: (20605)..(20782)
<223> OTHER INFORMATION: exon 10
<220> FEATURE:
<221> NAME/KEY: exon
<222> LOCATION: (22494)..(22675)
<223> OTHER INFORMATION: exon 11
<220> FEATURE:
<221> NAME/KEY: exon
<222> LOCATION: (24488)..(24703)
<223> OTHER INFORMATION: exon 12
<220> FEATURE:
<221> NAME/KEY: 3'UTR
<222> LOCATION: (24488)..(24703)
<223> OTHER INFORMATION:
<220> FEATURE:
<221> NAME/KEY: 5'UTR
<222> LOCATION: (749)..(979)
<223> OTHER INFORMATION:
<220> FEATURE:
<221> NAME/KEY: mutation
<222> LOCATION: (5158)..(5158)
<223> OTHER INFORMATION: T->A
<220> FEATURE:
<221> NAME/KEY: mutation
<222> LOCATION: (13539)..(13539)
<223> OTHER INFORMATION: T->C
<220> FEATURE:
<221> NAME/KEY: allele
<222> LOCATION: (916)..(916)
<223> OTHER INFORMATION: T
<220> FEATURE:
<221> NAME/KEY: allele
<222> LOCATION: (1022)..(1042)
<223> OTHER INFORMATION: Leucine stretch - insertion CTG
<220> FEATURE:
<221> NAME/KEY: allele
<222> LOCATION: (1116)..(1116)
<223> OTHER INFORMATION: T
<220> FEATURE:
```

```
<221> NAME/KEY: allele
<222> LOCATION: (1120)..(1120)
<223> OTHER INFORMATION: T
<220> FEATURE:
<221> NAME/KEY: allele
<222> LOCATION: (1137)..(1137)
<223> OTHER INFORMATION: T
<220> FEATURE:
<221> NAME/KEY: allele
<222> LOCATION: (4824)..(4824)
<223> OTHER INFORMATION: C
<220> FEATURE:
<221> NAME/KEY: allele
<222> LOCATION: (7464)..(7464)
<223> OTHER INFORMATION: A
<220> FEATURE:
<221> NAME/KEY: allele
<222> LOCATION: (13327)..(13327)
<223> OTHER INFORMATION: C
<220> FEATURE:
<221> NAME/KEY: allele
<222> LOCATION: (13349)..(13349)
<223> OTHER INFORMATION: C
<220> FEATURE:
<221> NAME/KEY: allele
<222> LOCATION: (13406)..(13406)
<223> OTHER INFORMATION: A
<220> FEATURE:
<221> NAME/KEY: allele
<222> LOCATION: (13559)..(13559)
<223> OTHER INFORMATION: A
<220> FEATURE:
<221> NAME/KEY: allele
<222> LOCATION: (13626)..(13626)
<223> OTHER INFORMATION: A
<220> FEATURE:
<221> NAME/KEY: allele
<222> LOCATION: (13632)..(13632)
<223> OTHER INFORMATION: G
<220> FEATURE:
<221> NAME/KEY: allele
<222> LOCATION: (13753)..(13753)
<223> OTHER INFORMATION: A
<220> FEATURE:
<221> NAME/KEY: allele
<222> LOCATION: (13781)..(13781)
<223> OTHER INFORMATION: T
<220> FEATURE:
<221> NAME/KEY: allele
<222> LOCATION: (13932)..(13932)
<223> OTHER INFORMATION: G
<220> FEATURE:
<221> NAME/KEY: allele
<222> LOCATION: (13993)..(13993)
<223> OTHER INFORMATION: C
<220> FEATURE:
<221> NAME/KEY: allele
<222> LOCATION: (19444)..(19444)
<223> OTHER INFORMATION: C
<220> FEATURE:
<221> NAME/KEY: allele
<222> LOCATION: (19576)..(19576)
<223> OTHER INFORMATION: C
<220> FEATURE:
<221> NAME/KEY: allele
<222> LOCATION: (19657)..(19657)
<223> OTHER INFORMATION: A
<220> FEATURE:
<221> NAME/KEY: allele
<222> LOCATION: (19697)..(19697)
<223> OTHER INFORMATION: G
<220> FEATURE:
<221> NAME/KEY: allele
<222> LOCATION: (20845)..(20845)
<223> OTHER INFORMATION: T
<220> FEATURE:
<221> NAME/KEY: allele
<222> LOCATION: (20846)..(20846)
<223> OTHER INFORMATION: G
```

-continued

```
<220> FEATURE:
<221> NAME/KEY: allele
<222> LOCATION: (22769)..(22769)
<223> OTHER INFORMATION: G
<220> FEATURE:
<221> NAME/KEY: allele
<222> LOCATION: (24633)..(24633)
<223> OTHER INFORMATION: G

<400> SEQUENCE: 3
```

| | |
|---|---:|
| ctggatgctt gtccagttga tttcttgaac atggtgtgta aaaggaatct ttgcaaattg | 60 |
| aatcttctgg aaagctgagc ttgtgcctac catagaattc tgaatgtacc tatatgacat | 120 |
| ctttgcaaac ttaaaacctg aatctttgta gtataaatcc cttgaaatgc atgtaggctg | 180 |
| gacatcaaaa gcaagcaatc tcttcaagga gcagctagtt ggtaaggtca gtgtgcaggg | 240 |
| tgcataaagg gcagaggccg gaggggtcc aggctaagtt tagaaggctg ccaggttaag | 300 |
| gccagtggaa agaattcggt gggcagcgag gagtccacag taggattgat tcagaagtct | 360 |
| cactggtcag caggagacaa ggtggaccca ggaaacactg aaaaggtggg cccggcagaa | 420 |
| cttggagtct ggcatcccac gcaggtgag aggcgggaga ggaggagccc ctagggcgcc | 480 |
| ggcctgcctt ccagcccagt taggatttgg gagttttttc ttccctctgc gcgtaatctg | 540 |
| acgctgtttg gggagggcga ggccgaaacc tgatcctcca gtccgggggt tccgttaatg | 600 |
| tttaatcaga taggatcgtc cgatgggct ctggtggcgt gatctgcgcg ccccaggcgt | 660 |
| caagcaccca caccctagaa ggtttccgca gcgacgtcga ggcgctcatg gttgcaggcg | 720 |
| ggcgccgccg ttcagttcag ggtctgagcc tggaggagtg agccaggcag tgagactggc | 780 |
| tcgggcgggc cgggacgcgt cgttgcagca gcggctccca gctcccagcc aggattccgc | 840 |
| gcgccccttc acgcgccctg ctcctgaact tcagctcctg cacagtcctc cccaccgcaa | 900 |
| ggctcaaggc gccgccggcg tggaccgcgc acggcctcta ggtctcctcg ccaggacagc | 960 |
| aacctctccc ctggccctc atg ggc acc gtc agc tcc agg cgg tcc tgg tgg | 1012 |
|                                        Met Gly Thr Val Ser Ser Arg Arg Ser Trp Trp<br>                                     1                5                     10 | |
| ccg ctg cca ctg ctg ctg ctg ctg ctg ctc ctg ggt ccc gcg ggc<br>Pro Leu Pro Leu Leu Leu Leu Leu Leu Leu Leu Gly Pro Ala Gly<br>             15                   20                   25 | 1060 |
| gcc cgt gcg cag gag gac gag gac ggc gac tac gag gag ctg gtg cta<br>Ala Arg Ala Gln Glu Asp Glu Asp Gly Asp Tyr Glu Glu Leu Val Leu<br>        30                      35                     40 | 1108 |
| gcc ttg cgt tcc gag gag gac ggc ctg gcc gaa gca ccc gag cac gga<br>Ala Leu Arg Ser Glu Glu Asp Gly Leu Ala Glu Ala Pro Glu His Gly<br>    45                     50                     55 | 1156 |
| acc aca gcc acc ttc cac cgc tgc gcc aag gtgcgggtgt agggggtggga<br>Thr Thr Ala Thr Phe His Arg Cys Ala Lys<br>60                        65 | 1206 |
| ggccggggcg aacccgcagc cgggacggtg cggtgctgtt tcctctcggg cctcagtttc | 1266 |
| cccccatgta agagaggaag tggagtgcag gtcgccgagg gctcttcgct tggcacgatc | 1326 |
| ttgaggactg caggcaaggc ggcggggag acgggtagt ggggagcacg gtggagagcg | 1386 |
| gggacggccg gctctttggg gacttgctgg ggcgtgcggc tgcgctattc agtgggaagg | 1446 |
| ttcgcgggt tgggagaccc ggaggccgag aagggcgag cagagcactg ccaggatatc | 1506 |
| ctgcccagat ttcccagttt ctgcctcgcc gcggcacagg tgggtgaagg agtgaatgcc | 1566 |
| tggaacgtac tggaactgc accaggcaca gagaaagcgg gcttgccatt atagtgggtt | 1626 |
| ccgatttggt ttggaaaaca tgggcagcgg agggtggagg gcctggagag aaggccctac | 1686 |

```
ccgagacagg ggcggggtgg gaaggacggc agatgctggg agcacgaggc aatttctta      1746
tgacacagaa ctcatgctct agtattccat ctgtttcagc cgaagaaaag aaccagctga    1806
aggggcaggg gagaagggc ggaggtattc tcgaggccca ttggcgtcct ttaggactca     1866
ggcagggaag ggcccttggt gctctggagc cggaggtggt gcgcctggta ctgggacccc    1926
ggagctgagc ccggcgcctc agcccacctg gctgtctgcc gaccgtgtgc ggggcgagtt    1986
tgctcaacaa ctctgccagc ttctggccct caggctgtgg gaagcttctt cccggggcga    2046
gaccactagc ttttctaag tattaccagc ccaggacttg gctgaggttc tgtgtccccc     2106
agcttggagt cagatgtggg gttgaatctt ggcttcctct cactagctgt ggtgcttgac    2166
aagtcactta tccttgagcc tccattgcct aatctttaaa agggaggtga caatcgtccc    2226
tacggctcag tggcagcaga tggggagatg aagggaaagt tctgttgacc atgagtgaac    2286
ttacaatgca agccccgggg ggatcacttg cagttttgtc cctgtctgca gtgtgacctg    2346
ttggtgacat tgtctttgct ccaaaccaca gctcctgggg cagaggggaa aattctgcca    2406
ctcacagctg cctgcccacg cttctgtctg agtgtgctgg gtggcaggat ggcaagtcct    2466
tactcagctc agtatagccc tcttccttgt tccctgagcc tttgactttc tcagggatg     2526
ttgtggggtt gtggccagga taagaaaggg catttcaagt taccactgct ccaaaacaac    2586
tgttctggaa atagtgagta ccccatcctg agaggtgagt aagcagaggc tgtatgacca    2646
cctgaaccaa gcccttgagg atgtttcttc tctggtggaa gtttggaaca ggagcctcct   2706
caagttcatt tattcattca ttcaatggtt attttgtggg aatcgaattt agaatgaaaa    2766
tatttttgg caagcagaaa ataatttta gaccaatcct tttcttttag tcatgagaaa     2826
ctgaggccca gagagaggag gtcaccccag gtgcattaga actgggtttc cagaactgac    2886
actccactgc acagagtact ctcccaattc attcaatttt tatttagcgg aaggcatttt    2946
cagatgggtc tttgaagcat tagtaggagt tcagcgatga tggtgtcatg agaattttat    3006
tctaggatta ggaggtacca tgaacaaaga tacagagctg ggaaaaccag aggtggaaga    3066
taaggagcac atgtccacag ttctttttct tttttttttg agatggagtt tcgctcttgt    3126
tgcccaggct ggagtgcaat ggtgcagtct cagctcactg caacatctgt ctcccgggtt    3186
caagtggttc tcctgcctca gcctcccaag aagctgggat tacaggtacc tgccaccacg    3246
cccggctaat ttttgtattt ttagtagaga aggggtttca ccacgttggc caggctagtc    3306
gcaaactcct gacctcctca gtggatccga ggaggtgatc ctcccgcctc agcctcccaa    3366
agtgctcgaa ttacaggtgt gagccaccac gcctggcctc cacagttctt tatccaccgt    3426
ctgaaatgta aaatgttacg aaaaccaaaa gttttttttg tgatttattt gatggtagca    3486
cctgacgtga actgacatga gattattttt aatttagttg tgtgaatatg catattcata    3546
tattttgctg catagattac agtatgcagc tccagattct tccaagcaga ctctgattgc    3606
ccattactgc ctttctaaaa tccaaacaag ttctgaggtt caaaaccgat ttggccctaa    3666
ggctttgggt aaagggggtg gactctgttc tactctgact ggagtccaag atgcatatat    3726
acagagatat gggtgatggg gctgcaaggt aggttgaggt aggggccaag gaggagcatg    3786
gagtttggac ttgattcatg aggctgtggg gagccagtga aggttcttaa gcaggtatgt    3846
ctgcctgaga gcagttggag cagacaagag ctaaaaacca aacaaatcac catagatagt    3906
ggctgctata atttgtttgt cccctccaaa tctcatgtgg aaatttggtc ctcagtgttg    3966
gaagtggggc ctaatgggag gtgtttgggt catgggggag gaaccctgt gaaaggcttg    4026
gtgccgtcct tgtgataatg agtaagttct cccgctatga tttcccttga aggctgatta   4086
```

```
ttaaaaagag cttggcacct ccctctcttc tctcttgctt cttctcttgc catgtgattg    4146
atctctgcac atgtaggctc cccttcacct tctgccatca gtgaaagcag cttaaggccc    4206
tcaccagaag cagatgctgg tgccatgctt cctggagagc ttgcagaatc atgagctgaa    4266
taaatccctt ttccttgtaa attactcacc ttcaggtatt cctttatata gcaacacaaa    4326
aggactaaga cagtggcctt gacttttctc tctctttaag aagtgttgcc tttgctcact    4386
tagtcatccc ttctgcctgc atttgtagag catctggatg ggagatttat ataaccgtca    4446
ctcttgactt tcccagcagg cctatgtcat aggtactgtg gtctctacaa tacagcagag    4506
gtatctgagg ctccgagagg ttgagtgact tgctcatggc tgcacaacca gtaaatattg    4566
gagctggaat tcaggtccac ggtttcctgg ctccaaagcc catgattttt tccctcaatt    4626
tattctgact ggggcatggg ggaggggtg gcctttgggc agggccacca ggagcgacca    4686
ggcccgtaga gagctgggtg caggtacaga ggaaaacctg ttgtcgagtg tggcccgtag    4746
ttcccatttt tgcctgaatg gcacatttga aagtgttata taaccatgtg aataataata    4806
gttggcctat atgagttttt taatttgctt tttggtccgc atttggtaac ttctttatca    4866
tctactatac tctgttgtgt ctcttttgtt gtaatttgta agtaggggtg agataaagta    4926
cacctagggt ttgctgggtt tcttccatgt catcatgttc ctccttgcat ggggccag     4984 gat ccg tgg agg ttg cct ggc acc tac gtg gtg gtg ctg aag gag gag    5032
Asp Pro Trp Arg Leu Pro Gly Thr Tyr Val Val Val Leu Lys Glu Glu
 70              75                  80                  85 acc cac ctc tcg cag tca gag cgc act gcc cgc cgc ctg cag gcc cag    5080
Thr His Leu Ser Gln Ser Glu Arg Thr Ala Arg Arg Leu Gln Ala Gln
             90                  95                 100 gct gcc cgc cgg gga tac ctc acc aag atc ctg cat gtc ttc cat ggc    5128
Ala Ala Arg Arg Gly Tyr Leu Thr Lys Ile Leu His Val Phe His Gly
        105                 110                 115 ctt ctt cct ggc ttc ctg gtg aag atg agt ggc gac ctg ctg gag ctg    5176
Leu Leu Pro Gly Phe Leu Val Lys Met Ser Gly Asp Leu Leu Glu Leu
    120                 125                 130 gtgagccacc cttttgggaa atggcacttc ctgatagggc tgggccactg catatacact    5236
ggggactgtg cttagtaggc ccattgctga aaatcagaag gggacagcaa gtatgtattg    5296
agcacttatc gggtaccaag cacagtaact actggctttc tgtatagaat tcccttaag    5356 cctggccatg ccccagtggt acgtctatct tcatttgaaa gacgaggaga ctgaagttca    5416
gaggggacca cacagacagc tagggtaga gcctggatca aacccattgg tctgcctgcc    5476
agccattctt gtgccaatgc atctgctgcc tacggaaacc tgtagggaca aggccctggg    5536
atgttcagtg gagcctgagt cattttataa aaaagcatga ctctagggtc caaaattcct    5596
ttgaagctgt tgctatccag agtgaagtcc cttctttagg acagggtggc cctcctccct    5656
cctggatgtc acatcttcgg tggaggggca gaaaggggac tgggtattct cctcaccctg    5716
gccctagtgc ttcaaatctt aaaaaaacgt ttttatttgt gcttctgcac caccttctag    5776
cccacctcgt ttcctggcct ctaacttgat gagagcgtgt gtcattttca cactgattct    5836
ccacatggca ggcggtgctt cttagcctcc tgcagacagt gaggccccac ggtcttgtcc    5896
aaggtcacac agcgtgtaat gggcagggtc agagtctgga gtctggacct gggtctccta    5956
gctgcactgc actgctgccc catgggttaa tcagctcagc ataccgtggc tgaacagcta    6016
cctcatacca aggcctgtgg cgccatgaca gggattgaca gggtccctgc cttggaaacc    6076
cgtagtctaa gtagaggaga ctgacaagtc aatgccttcc atcagtctgc tcaacacacg    6136
```

```
tttaccaagt gcctactgtg tgctgcagag gcgaagatga cacagctcag gcctttccct    6196
tgagcttaca gttcaggagg agagactgac cagtgactgc cagtacagtt gactatggga    6256
caatgtgctc agccttgggg agagacgaag aaggtacccg tatagcacca gatgacaggc    6316
acgagcccca caggccaggg cagctgctca gaggagagta ggccaagcag aaggcaaaca    6376
gaaggctgca ggcatttgcc atcgagagct ggacttcaaa ctgggcatca taccagcctg    6436
ggttcgagtc ctgcccagcc ccttattggc tgtctaaccc tgagcaaatc ccttcacctc    6496
tctgagcctc attcctctat ctgtaaacca gttataataa ttggaacatt catttaagga    6556
ctaaatgagg tcgtgaagca ttcagcagat gctaggtacg gaaactcgct gaagtggggg    6616
caggttaaga agcctctggg gatacgaagg catccaggga ctagttgtgg caggaggctg    6676
ttaccactta ggtctgaagg gtaaggagag ggaatagctt tccctctgcc cagttggagc    6736
cggtggcatg gaggagaggc tgcctgtggg gaatcacccg agggttcacc gctgccatgc    6796
gcagggagtc aggaggtagg gagggagtgg ggcagatgca caccattttt tttttttttt    6856
gagactctgt tgcccagact ggagtgcagt ggtgccatat ctgcacctct gcctcccggg    6916
ttcaagctca ctgcaacctc tgcctcccgg gttcaagcga ttctcctgcc tcagcctccc    6976
gagtagctgg gactacaggt gtgtgccacc atgcctggct aattttttgta tttttaatag    7036 agatggggtt tcaccatgtt ggccaggctg gtctcgaact ctcgacctca ggtgatcccc    7096
cacctcggcc tcccaaagtg ctgggattac aggcgtgagt caccgctccc agctgctgat    7156
gcactcttgt ccttctaact cctgctagtc cctcccattg gctgagccca actggaagct    7216
ttgcaaggga gctggtgctg cagtttgcac tgagcaggct ggagaaggct ggagaataga    7276
ctaggggaca aaccgaattg ccagtgctgt tatgtcatga tttaggcatg gagtccaggg    7336
cctgagcttc actccatgtc catcctgccc agagccttgg cacagcctgg ctcccagaca    7396
agatgtcaag ttcagaatcc ttcctaaaag gaatcctcta tgccagaccg tgttgcaggg    7456 atatggggt gctgggctcc cagcctgatc aaggagcgag aaaactcagg ctcctagtct    7516
gtcctccggg gcactagcag ggacaaggtg ggaggctgct gggctgggat gtggggacag    7576
gtttgatcag gtaaggccag gctgtggctg tgtttgctgc tgtccaaatg gcttaagcag    7636
agtcccccgg cctctctggc ttctgcag gcc ttg aag ttg ccc cat gtc gac        7688
                                Ala Leu Lys Leu Pro His Val Asp
                                            135             140 tac atc gag gag gac tcc tct gtc ttt gcc cag agc atc ccg tgg aac       7736
Tyr Ile Glu Glu Asp Ser Ser Val Phe Ala Gln Ser Ile Pro Trp Asn
            145                 150                 155 ctg gag cgg att acc cct cca cgg tac cgg gcg gat gaa tac cag ccc       7784
Leu Glu Arg Ile Thr Pro Pro Arg Tyr Arg Ala Asp Glu Tyr Gln Pro
        160                 165                 170 ccc g gtaagacccc catctgtgcc ctgccccacc ccatctgagc tgaatccatt          7838
Pro tgctctgccc tggcctggcc tccctgctgg tggtttccac ttctcggggg gctttgggac    7898
tcagcacctc cactgacccc ttttttttctg tcccatcccc atcccctgca gcccccactg   7958
cctgccttcc tgttgcccca caaatgcaaa agtcttgcct taaatgatcc tcttttcctc    8018
cttttctctt gttttccttt tctcaccatt tggaatggcc cagcaggctg cacttaccttt   8078 ggaaggaggg ttcatctgat ggtgactcta cctagggccc ccaggcctct ataactccca    8138
gtgccctgca gactggacca gatcctttaa tgggatagac acaaccctgt ctgggatgcc    8198
tctgcctacc ttcctgtttt gctgctccac ctgcctccag ctccgtttgg cttcctgggg    8258
```

```
ctccctgcct gggccacttt gtgtcttccc tctaggcctt tctttccact gttccctctg    8318
cctggtgtgg cctggctatg aagggaggg agcaggagcg gccatggaaa acggtctgca    8378
ttctagcagg gacttgcagg tggcaattca gtcggggaag actctagatg cacctggcct    8438
gaggagagaa tgaagggttc tagttggact gtgttaagtt tgaggtgccc atggtgtgag    8498
gtctggagct cagcgcagag atgatgcaat gtggtgggtc catgcaacat ggtgccagga    8558
cgcagagctt ggggtgaact cagctttcac cccttaccgg ttctcgtggg atcttgggaa    8618
gccactttct tctatgagct ttgtcgttct tgtctgtaaa atgggcacat aaccctgtcc    8678
ctgtccttct cacaggttgc tgtgagactc aatgagttg aaggatgtgc agatgctttt    8738
ggaagtgaaa agttgggggg ctactgtgtg actttgcata cacccaaact gtgtgacctt    8798
gcatatgtct gagttgctgc cattgcaaca gatcagagct ggtgggctgg gtgtggagaa    8858
agggtttgtg tgggggacat cctctggcaa gggtggcagc agcagaagtg aggggcctgg    8918
tcggtcatgt gtgctgaccc ggcctgggca gcctgtggcc aggagagga cagctcctct    8978
gtaggaagag cgtgttcctt tccaaccagg tgagacctct tcagtggagc cctggagccc    9038
cctgtactcc acatcagtgc ctcagggacc tcccggagca ggctaatatc agagaccaag    9098
agggacactg gcagaggatc acagagaccc cagtccaggc agggactgag aagatcttgc    9158
cccctaagtt agtttcctag cactgctgtg acaaaatacc ccccctcgg ttggaacaag    9218
ttgattctct gcagtcctgg aggccagaag cctgaatcag tgtcggcagg accactttct    9278
cccgggggc tccagggaga agcttctctt gcctcttccg tgtcccaaca gcggcagcac    9338
accaatccca gcctctgtct tcacacagcc ttctctgtgt ctctctcctc ttcattgtct    9398
cataaggaca cttgtcattg gatttagggc ccactggatc ctccaggatg atctcatgtg    9458
gggaaccta accacatctg caaggaccct ttttccaaat aaggtcacag ccacagtttg    9518
tgggggttag gatgtgagtg tatctctttg gcagccactg ttccctcctc tcccttgggc    9578
cagaagcaga cgtggggccc tttcttcccc ataggatgcc catggattgc ccccttccc    9638
gcttcccccg agcgtctgtg ggaggtggca ggaatggcag gcaggtgtgt ggaaccccctt    9698
ctggagtcat atcaagggct tggctggagg aagtcctcct ggagctgttg ggctggcatg    9758
gggcaggctg gctgggccca gcagcagctt cttcattcat ggggaggcca caagcatggg    9818
ccctagagct ggctgccgcc ctcaaaccca gaccctgcac tcttaactgt gtgaccttgc    9878
atacgtcact cacccctctct gatcttcagg ttcctctgca aagggaggt aatgataacc    9938
ctcactctgg ggggctgttt ggagggttaa atcagttatt gctgtagcat gcatttctct    9998
gtcaggtatt gagtgaggtg ctgtgatttt agccctgcat ttttcttttc ttaccattca   10058
ataataacgt tttgagcacc ctctgtgcgc caggcaccat attaggtgct ggggatacaa   10118
atgtgaatga aatgaatgtg gtctctttcc ccaacagtgt atccagaaga ttaatccatt   10178
ccttaaacaa atgctacttg acacagatta gttctgata ggctgagagc tctgaaggag   10238
tgcaggcagc tgcgagcctg tgtatccagc agaaggatca ggaaaggatt cctggaggaa   10298
gcgctgttct agccaagacc tacgggggca ttattaacca ggcaaagggg acggtgtcca   10358
agcagtggaa tgaacgtgga ttgaagctgt gaggcaggag ggagtgtggc ctgtgcagaa   10418
gggaccgagg ctggtgagac cagcagggcc tgggtggcct ccaggtcaga tgtgaaagga   10478
agaacttggc cacagtctga gcttctcagg cgtatggcag ggctgcctgg tgagagggaa   10538
tgagctccct gctctggagg tatgcaagca ggactgggct ctcacctgcc agaggccaca   10598
gagctttcca gaggctggaa gaggccactc caaggcctct ttgcccctga gagtggtggc   10658
```

-continued

```
tcttcttgag gccaccttgc cacgctgtca cagggaacta gcagccctg cctcacccgg    10718 gggtttggaa gatagaggga ggcctaggaa gggccctgtg tctcatccga gctgggcccc    10778
tttccagcct ctcactggaa ggaagcccaa ggatgttcct gtgggggctt ttaccaggcc    10838
cacctgccct ctgctggcca tgcttgcagc ctcctgaccc tgtcccagca ggacagtggg    10898
ctggtgtgag cggcaggaa ccgcctgcac ttagaaggtg tggggctgcc tccccgagct    10958
tccatctgcc gctggggcca caccccaggc ccagggatgg gaccccatag tggtcacatc    11018
atcttgcagc agaacccagg tacagctcct ggagcagatg gtggtcccaa gcacgggtgg    11078
gaccagaaag gactctcacc tgggctaact cagctgcagc ctcagttccc tcctcacaca    11138
cgaggaacat ggactggaag cctgcccagc aggccttctg ctcgatgtgc gttgtgtggc    11198
ttacgtccag ggagggaagc agcctctgtg ctgtcttcta gataagcctg tattccccgg    11258
gctgtctgcc aatgtatcca gttgtcccgt cagcctggaa gctctgaggg aaaaccttgg    11318
gctgcttcct gagcacctgt atcccctgca gccagcccgg ggcctctgct aggagcagac    11378
tgagcatggc ttatgggcct ggcaccatct ggcctctgcc caccttgctg gccttgtctt    11438
gtgtctgccc cttcgacatt ccatagccca gctcaatatc tagtggttcc tctagggtgg    11498
cgagcactgt ttggtctcca gatgtcttca ggtcggagct cacagcgctc tcagccaccc    11558
cttcccagtg tagcaccggg cacatggtag atgcctattg atgagtgaaa gctcctaaca    11618
cactcagaga gcaaggactc cgcctcatcc cacagcctgg gaggagaggc agactgccaa    11678
ggacctgctc agcatgctac agaagaaacc aaagtgccca cgggactgat cagtggagct    11738
tcctgccgag actggaggcc ttagggcagg gtagacagtg tgtgtgcagg ctggggactc    11798
acagttcgga ctgtgcccag acctactagc atagtgggtg ggtgggagga tgcgggactg    11858
ggggccgacc ttgcctgaaa ttcatgtggg atctcagagc agccactgaa ttgctctgta    11918
gggggctaaa tagtggcccc cacagataca cacacccaga cagagcctgt gagccagacc    11978
ttatttggag aaaaggtctt tgtagatgta attaagcatc tcaagatggc atcatctgga    12038
ttatgcggtg ggctgtaagt cctgtgatgt gtctttatga gagaaaggca gagggagatt    12098
tgacacacac aggagggggcc acgtggagac agaggtggag attggagaaa tgtggccaca    12158
agccagggaa caccagcagc caccagaagc cggaagacgt gaggcagggt tcttcccaga    12218
gccttcgctg ctgagtctgg gaatttgtta ccgaagccat aagaagtggg tacacgccct    12278
gagcctccca cacttgctca cctgtcctga gatgagaatc tctactctgc agcatatttg    12338
gaggatcact gcgggggcca cagaggtgct gttcagatgg cacttcagaa gactcaggag    12398
accctggggc aggagcagtt tgactgacag cccagagggc tgccctctga ttccacctga    12458
ggccctgctt ttcctggctg caggggttcc agggccaggc catttccgct ggcgcaggac    12518
tctgctagca gcaacctgcc tgaagtcttc ctttggcctg gctgagagtt tctgagacct    12578
gcgctggagc ggaggtgctt ccttccttgc ttccttcttt cctctctccc ttctccatcc    12638
agcaggctgg acctgcctgg catctgtgag ctctccctac tttctcctat accctaacct    12698
ttgtcctgca tgggcgactc ccccagtgag tctcttgcag cttttacccc agtgcctgct    12758
tcttggagaa tccaaactga tccagttagg gatgataaag tgtagggtag gtgctcggtg    12818
actgttttct ctgaggttgt gactcgtgtg aggcagaagc agtcccgtg agccctcctg     12878 gtatcttgtg gagtggagaa cgcttggacc tggagccagg aggccagac atacatcctg     12938 tccgagctgc agcttcctgt ctctaaaatg agccggccag cgcaggtggc cagacatcac    12998
```

```
tgttattctc ctttgagtct ttaaatcttg ttgtctttct tgcagactcg gtgagctgtg   13058
aaaggctata ataggggctt tattttacac tttgatacta tttttgaac attcatatta    13118 ttgttagata ttgatattca tatgaaggag caggatgact tgggtccttc ttggcagtag   13178
cattgccagc tgatggcctt ggacagttac ctgccctctc taggcctccc tttccttgtc   13238
tatgaaatac attatagaat aggatgtagt gtgtgaggat ttttggagg ttaaacgagt    13298 gaatatattt aaggcgcttt caccagtggc tgggatgtgc tctgtagttt gtgtgtgtta   13358
actataaggt tgactttatg ctcattccct cctctcccac aaatgtcgcc ttggaaa     13415
```

| | | | | | | | | | | | | | | |
|---|---|---|---|---|---|---|---|---|---|---|---|---|---|---|
| gac | gga | ggc | agc | ctg | gtg | gag | gtg | tat | ctc | cta | gac | acc | agc | ata | cag | 13463
| Asp | Gly | Gly | Ser | Leu | Val | Glu | Val | Tyr | Leu | Leu | Asp | Thr | Ser | Ile | Gln |
| 175 | | | | | 180 | | | | | 185 | | | | | 190 |

```
agt gac cac cgg gaa atc gag ggc agg gtc atg gtc acc gac ttc gag   13511
Ser Asp His Arg Glu Ile Glu Gly Arg Val Met Val Thr Asp Phe Glu
                195                 200                 205 aat gtg ccc gag gag gac ggg acc cgc ttc cac aga cag gtaagcacgg   13560
Asn Val Pro Glu Glu Asp Gly Thr Arg Phe His Arg Gln
            210                 215
```

```
ccgtctgatg ggagggctgc ctctgcccat atccccatcc tggaggtggg tggggactgc   13620
caccccagag cattgcagct gtactcctgg gttgcacccc cccagctgtc actgtcccct   13680
ccctgccatc agttgtggga agggcgttca tccatccagc cacctgctga tttgttatag   13740
ggtggagggg gggtctttct catgtggtcc ttgtgttcgt cgagcag gcc agc aag   13796
                                                    Ala Ser Lys
                                                            220
```

```
tgt gac agt cat ggc acc cac ctg gca ggg gtg gtc agc ggc cgg gat   13844
Cys Asp Ser His Gly Thr His Leu Ala Gly Val Val Ser Gly Arg Asp
        225                 230                 235 gcc ggc gtg gcc aag ggt gcc agc atg cgc agc ctg cgc gtg ctc aac   13892
Ala Gly Val Ala Lys Gly Ala Ser Met Arg Ser Leu Arg Val Leu Asn
240                 245                 250 tgc caa ggg aag ggc acg gtt agc ggc acc ctc ata g gtaagtgatg     13939
Cys Gln Gly Lys Gly Thr Val Ser Gly Thr Leu Ile
255                 260                 265
```

```
gccccagacg ctggtctctc tccatctgga cctggcctgg gaggtggctt gggatgggcc   13999
cagggagagc taatgtctcc taaccaagaa tgctgtggca gcctctgccg cagagccaga   14059
gaaccagagt gccaaggctg cagggttcc cagtggccac gagtgcagat gaagaaaccc    14119
aggccccaag agggtcatgc aagtagccca gggagttcag ccttgaccct gggtcaatga   14179
cctttccaca gttccacact gctccccttt taaaatccgg tgatgtcttt atgtcttttg   14239
ttatgttatc ttcaatgtgg agggactcga ggtgatctaa gcaaactttt tctatcttct   14299
gcttgcatac ctctgagacc aggggactca ctcacttgca tgactgggcc ctgcaggtca   14359
cactggccag gcagatgtgg tggaggaact ggcagaggac ttttttctaga ctgtgactac   14419 atttagtcca cccagcggcc cccctatgaa gtccagttga aactaggac tctggggcc     14479 tgtggacaga aagagggag ggttctctcc cttactgact tccttctgtg gccagacatt    14539
gagcaaggcc tctgtacagc atgtcctggg gctggccttg ccgtagctgc taaatagttg   14599
acgaaaccag tccagagagg ggaggtgact gccagggtca cacagctcaa gctggggaac   14659
tcgctgggaa aactgtcagc tctgggcagc agcttgactt ccattgtaag ccccagcccc   14719
cagggtcaaa cactggctct ggtgctggca gaggcagccc actagcctgt ttcaaaggct   14779
gagaaggccc aggagtctgc cctgtgctcc accagttctg ccctgagact ttcctacaga   14839
gtacaggttt tgatgttcag ttttaaaggc aagaatcaat aaccttctgc cccatcaggt   14899
```

-continued

```
gacccttgt gcctgtccca cccctttatt gactgacctc ggctcagtca ggtcagttcc      14959
tgaaggtcag tgtgtggagg ggaggctgtt ctttcccaga aaggccttcc ccaggcctgg      15019
tgctctggcc tctggaggac ttcctggaga agtcccttct ttgggtccca agtcagtgta      15079
tgggaagccc ttattgcatg acctggcacg gggtagggc tcaacagtca ctattgcctt      15139
ccttgccact gccatttcct cctctgtaag caggtgattg tgtgtccagt ctgagcacag      15199
agataagcac acagcaggtg cttaataact agcagctgta ggctgggcgc ggtggctcat      15259
gcctgtaatc ccagcacttt gggaggccga ggtgggcaga tcacctgagg tcaggagttc      15319
gagaccagcc tgttcaacat ggtgaaaccc cgtctctact aaaaatacaa aaattagcca      15379
ggcatggtgg tgggtgtctg tatcccagct acttgggagg ctaaggcagg agaatcgctt      15439
gaacccagga ggtggaggtt gcagtgagct gagatcgtgc cactgcaatc cagcctgagt      15499
gatagagcga gattccatct caaaaataaa taagtaaata actagcagct gtaaatgtgg      15559
ctgttgttct tcacctccac actcagtgcc actccactcc ctccctccgt ggtgtgaggg      15619
gcctcactag ctgtctccta ggaggagcat ggctgtgaga ttccagctcc atccttgacc      15679
acggctcctg gagacatctt agaggccagg atccagaagg ctcccacacc ccatttgaca      15739
ggggagaagc tgtcagttcc aggtccccct gcacatcagg gccagagctg cgttaggcct      15799
ccagtctcca ggccactggg ccagagctca caggctggca gagggttaga actgttactg      15859
gtggctgggt gcactggctc acgcctgtaa tcttagcact ttgggagggc aaggcgggag      15919
gatcatgagg tcaggacatc gagaccatcc ttgctaacac ggtgaagccc cgtctctact      15979
aaaactacaa aaattagcc gggcgtggtg gcaggcgcct gtagtcccag ctactcagga      16039
ggctgaggca ggagaatggc gtgaacccgg gaggcggagc ttgcagtgag ccgagattgc      16099
gccactgcac tccagcctgg gcaatagagc gagactccgt ctggaaagaa aaaaaaaaa      16159
agagctgtta ctgttgacag tagcatgagg tagaccatgg cctgcaccaa aagggggagt      16219
ggagtgccac tgaggccaga aggaaccaca ccctcaaggg tggggagtta tggtatgggg      16279
ggtcctaggc atggagtctt ttaattcttt agacaatcct gggagcagct gtccctgttt      16339
cacagagggc ggggccacac agctggtgag tgggcagcca agactctgtt caagtttgtg      16399
tgggtccaac acttgcggcc acggtggagg ggcatctgag ccaggcctca gagagtggcg      16459
gggggaagtt gggtggggaa gtgtgcccct ctcattcctc tgaggctcat cctcttggtg      16519
cctctctttc atggaaaggg ataataaggt tattgtgagg atcccctgag ttcatatatt      16579
cagacgctta gacagagcca ggcacagaga agggcccggg gttggctagt ttgattgctg      16639
gtgtaattgc taatatcttc cagtttgtat tggtcaaggt tctgcagaga agcagaacca      16699
gtaggaggta tatattaaga gtttcaagct catgtgaccg tgcgggctgg caagtctgaa      16759
atccgcaggg caggccatgc aggctggcaa ttcctgcaga atttgatgtt gcaatactga      16819
gtcctaaggc agtcctgggg cagaattcct tcttccctgg gaggcctcag tctgttctct      16879
taaggccttc aactgattaa atgaggcctg cccaagttat agagagtaac ctgccttact      16939
ccgtcttctg atttaaatgt tagtcacatc taaaaaatat tttcgcagca gcatttccac      16999
tggcttttga ccaaacatca ggccacaaag ttgatcccca aaattaacca tcactctgtg      17059
cctgtaaggg aggggctggg aaggggagc aggtctcccc aagggtgac cttggctttg       17119
ttcctcccag gc ctg gag ttt att cgg aaa agc cag ctg gtc cag cct          17167
               Gly Leu Glu Phe Ile Arg Lys Ser Gln Leu Val Gln Pro
                   270                 275
```

-continued

| | |
|---|---|
| gtg ggg cca ctg gtg gtg ctg ctg ccc ctg gcg ggt ggg tac agc cgc<br>Val Gly Pro Leu Val Val Leu Leu Pro Leu Ala Gly Gly Tyr Ser Arg<br>280               285                    290               295 | 17215 |
| gtc ctc aac gcc gcc tgc cag cgc ctg gcg agg gct ggg gtc gtg ctg<br>Val Leu Asn Ala Ala Cys Gln Arg Leu Ala Arg Ala Gly Val Val Leu<br>                    300                    305                   310 | 17263 |
| gtc acc gct gcc ggc aac ttc cgg gac gat gcc tgc ctc tac tcc cca<br>Val Thr Ala Ala Gly Asn Phe Arg Asp Asp Ala Cys Leu Tyr Ser Pro<br>315               320                    325 | 17311 |
| gcc tca gct ccc gag gtaggtgctg gggctgctgc cccaaggcgc gggtaggggg<br>Ala Ser Ala Pro Glu<br>           330 | 17366 |
| cggagggcgg agggagggcg ggcgggcagg cgggcttctt gtggcacgtg ggcttcttgt | 17426 |
| ggcacgttcc tggaggccga acccttctgg ctttggaagg agtcgtcaga daccccgcc | 17486 |
| atgcgggagg ctgggagga aggggctcga aacctccatc atcgcagagt ctgaatagca | 17546 |
| gtggccccgc catgcgccca cgtagcggcg cctacgtagc cacgccccca cgccccgtcc | 17606 |
| tggccactct ccctcctgaa ggtcttctgg tacccgcccc ctccccatct ccatccccag | 17666 |
| gccctgcgtc ctctgcccaa tactctttgg gcctccctgt tgtccagctc tctccgcggc | 17726 |
| tccatgactg acaacttgag caaggctaat gtgaatggga gcggttgagg gctcagacct | 17786 |
| ctcacccgag gaacatccac agagtgtgcc gcatgcccgg tgcagtgtgg ctgcggggac | 17846 |
| acagacacgg agcctcggcc ctgaggagct gggggggcagt gaccgtccct cctctgaccc | 17906 |
| accactcctc cagtgtcagg acactgcggg tatctagggg aaggaatctt gttccacttc | 17966 |
| aagtctggaa cttcaagtct gtgtgtgtgc gtgcgcgcgc gcgcgttggg ggtgggggtt | 18026 |
| gcagagcaga tgcgtacctg acagcggtaa cctaggtccc cccggcctat caaggcttcc | 18086 |
| ctggcggccg aatttaaagg catcaagcaa acaaagccca acacatctct gccttgtcct | 18146 |
| ctcagttttcc ccccgtggca cttagaacca cttgatacac cgaatagttt ccggtctatc | 18206 |
| tcccccacta ggatgtaaac tccacagggg cattgggaat gctgcctggc tatggtaggg | 18266 |
| acagagggga gcaccagggc ggggcagggg tgccagagtt ctgcctgggc agtcagattt | 18326 |
| tccttaggag gggacatttg agtgggaccc aaacaggtgt atagcagttg tccagcccag | 18386 |
| ctggcaaggc ctgagtctgc ctctgcaacc cctctcttgg gctcctttct ctgccaccca | 18446 |
| cctcctcacc tttccag gtc atc aca gtt ggg gcc acc aat gcc cag gac<br>                         Val Ile Thr Val Gly Ala Thr Asn Ala Gln Asp<br>                               335                    340 | 18496 |
| cag ccg gtg acc ctg ggg act ttg ggg acc aac ttt ggc cgc tgt gtg<br>Gln Pro Val Thr Leu Gly Thr Leu Gly Thr Asn Phe Gly Arg Cys Val<br>345               350                    355 | 18544 |
| gac ctc ttt gcc cca ggg gag gac atc att ggt gcc tcc agc gac tgc<br>Asp Leu Phe Ala Pro Gly Glu Asp Ile Ile Gly Ala Ser Ser Asp Cys<br>360               365                    370                   375 | 18592 |
| agc acc tgc ttt gtg tca cag agt ggg aca tca cag gct gct gcc cac<br>Ser Thr Cys Phe Val Ser Gln Ser Gly Thr Ser Gln Ala Ala Ala His<br>                    380                    385                   390 | 18640 |
| gtg gct g gtaagtcacc accccactgc ctcggccacc gtgatgctaa cagcccttt<br>Val Ala | 18697 |
| ggcagtcagg gtctgtgccg ggacctccag tgccaggctc tgtgcagggg gaccagagat | 18757 |
| gaagtaggcc tgatggtgcc ttcaaggaca ctcagtctga tgaggaggc gagtgcacag | 18817 |
| agggaacacg aggtcagggc tgtattagag ggagcccaga ggaggcacct gcccagcccg | 18877 |
| agggtcagag aaggcatctt ggaggaggga catttgatcg ggagcttgat ggatgaatag | 18937 |

-continued

```
gagtttacct ggccgataag acagcaacta ccaaggctta gaggtgtgag aggaggctgt      18997
cttacctcac tgagtaagga ctgcaggcgg cttaccttcg agaagagagc ttagtgtctg      19057
tgtgcacgtg tgtttgtgtg tatgtgtgtg cgtgtgtgca ctggcaggag tccctgctg       19117 gggcaggagg gccgggccat caccatcttt caccattcac ccctgcacca ggc att         19173
                                                          Gly Ile
                                                              395 gca gcc atg atg ctg tct gcc gag ccg gag ctc acc ctg gcc gag ttg        19221
Ala Ala Met Met Leu Ser Ala Glu Pro Glu Leu Thr Leu Ala Glu Leu
                400                 405                 410 agg cag aga ctg atc cac ttc tct gcc aaa gat gtc atc aat gag gcc        19269
Arg Gln Arg Leu Ile His Phe Ser Ala Lys Asp Val Ile Asn Glu Ala
            415                 420                 425 tgg ttc cct gag gac cag cgg gta ctg acc ccc aac ctg gtg gcc gcc        19317
Trp Phe Pro Glu Asp Gln Arg Val Leu Thr Pro Asn Leu Val Ala Ala
        430                 435                 440 ctg ccc ccc agc acc cat ggg gca g gtaagcagga tggcagggtg                19362
Leu Pro Pro Ser Thr His Gly Ala
        445                 450 ggcaagtcca ggctggggct tgggaggtct gtgtgacctt gacagtctct cccttctccc      19422
ttgtctgtgt aaggaggatg atgccacctt aaataggatt aaatgagaat ggggctctga      19482
aagggctgtg caatatttc ataacgtgtt tttatagaga cagttgagta tgttcttaa        19542 gccctcctct ctcctaccat gaactaaaga tttttgtgga ggtcccctca ctcccagcac      19602
cccctcctca tcccaggccc ttttgca ggt tgg cag ctg ttt tgc agg act          19654
                              Gly Trp Gln Leu Phe Cys Arg Thr
                                              455 gtg tgg tca gca cac tcg ggg cct aca cgg atg gcc aca gcc atc gcc        19702
Val Trp Ser Ala His Ser Gly Pro Thr Arg Met Ala Thr Ala Ile Ala
460                 465                 470                 475 cgc tgc gcc cca gat gag gag ctg ctg agc tgc tcc agt ttc tcc agg        19750
Arg Cys Ala Pro Asp Glu Glu Leu Leu Ser Cys Ser Ser Phe Ser Arg
                480                 485                 490 agt ggg aag cgg cgg ggc gag cgc atg gag gtgactgtac ccctccttcg          19800
Ser Gly Lys Arg Arg Gly Glu Arg Met Glu
                495                 500 tgtgtgtgtg tgtgtgtgtg tgtgtgtgtg tgcgtgtcag tgctgggccc tcagggaccc      19860
ccagcaagcc cctccatcct ccagactcca gctcttctgt aagcttacag ggctggccag      19920
accaggagtg gggcactcct cacttcacgc ggctgggggc tgctggagag agccacagcg      19980
ggaagggttt cctagaggct gcaggacagt gctggatgga ttttcaatgc tcacctgggt     20040
gtgagcatgc ggcagggccg cgtgagggtc agcgatctgc tactctggac tcagccatct    20100
ctaggcccct ctcactcagg tgctccatgg ttctgggagc tgagaaatct caaaccagca    20160
aaaaagtgga attgatgttg atgctacagg atagtgcaca gatgccatct ggttgcagca    20220
ttttggtgga agggcagtgc ccagctagga gagtgaggag gggcaggcat ttctggcttg    20280
aggagatagg gtcttaatgc tcgtgtgaga ggcagagtgg gtggagtgga gctggctgga    20340
tccttgcttt ggcctcctgg atttctctct atctccattt tgaaaccact ctgtgtttgg    20400 aagaacttt gagtattcag agctgcccac tggcagaaca gtcttccttg gcaggagtg      20460 agctccttgt ccccagaagg ctgggtctgg ctggccctg gcaggacac tgatgagggt      20520 gcttgagttg atcctgtcta gtcccttct gtgttttcaa agcccattct aaagcagatt     20580
cccatttccg tctttgactc taag gcc caa ggg ggc aag ctg gtc tgc cgg        20631
                              Ala Gln Gly Gly Lys Leu Val Cys Arg
                                  505                 510
```

```
gcc cac aac gct ttt ggg ggt gag ggt gtc tac gcc att gcc agg tgc      20679
Ala His Asn Ala Phe Gly Gly Glu Gly Val Tyr Ala Ile Ala Arg Cys
            515                 520                 525 tgc ctg cta ccc cag gcc aac tgc agc gtc cac aca gct cca cca gct      20727
Cys Leu Leu Pro Gln Ala Asn Cys Ser Val His Thr Ala Pro Pro Ala
        530                 535                 540 gag gcc agc atg ggg acc cgt gtc cac tgc cac caa cag ggc cac gtc      20775
Glu Ala Ser Met Gly Thr Arg Val His Cys His Gln Gln Gly His Val
            545                 550                 555 ctc aca g gtaggaggct gggcttgccc tggggtgagg agggtctct ttctccttat      20832
Leu Thr
    560 gcacccactg cccacgaggc ttggtcctca caagtgtgat ccatgagact caagcctgac   20892
ttgcagttcc atactctggt tctgccactt ccatgccctt tgagcctggg caggtgacct   20952
tacttctcct catctcagct tcctcctcca taagagggaa aaaggtatta cctgcctcat   21012
tgtgttgcaa ggagatgggc agcatctagg gcactggcct ggagtatcgc aggtgctttg   21072
cctaaggtgg tgcagtccag gagaggcagc tccagagaga ggcccccggc tgggggtgaa   21132
aggagggcag acctcggttt gaatttcacc ctgccgctcg atagctgtgt gacttgggca   21192
aattacttaa catctctgta tgaggaaatg atgagtgcta agcacttagc ttagtgccgg   21252
gacaatataa attctagcta tcgttactat tgttttcatc acccgttgct ttaaaatcca   21312
gtctctggta taggcaacta ttgacgggct accctgtgtc gaaaacatgc ccaggcaggt   21372
agcaggaagt cacagatggg gacctcttgg ggcatcaagg gatggtgccc tgaggctgag   21432
ctgttctggt tgggtggagc atgagaggtc tgggaagaca gtgggactcc agcctggaat   21492
aagaggctca gagttgattc tcgtctgagc acgtccaggg gaaccactga gggtttggga   21552
acaggagagt gagggtgaga acctggttct gggcacagca ggctggcatg taggatggat   21612
gttcaggaaa gatgagcata gtcaggtggc tggtgcccct tgtccagggga gaggctccgt   21672
caggttcagg ggtcctggct tggagggaag tccgccatgc tctaatcacg ctccccttttg  21732
gaagtgctcg gccgatgagc tcacaggcac atgtcagttt gaagtcatgg aatctgactc   21792
catgaagcgc acctcaaaga gcaccatttt gcagctaagg gaactgcagg ctggacatgc   21852
tgagtggctg ccccgagccc ttgcagctag gacatagaga atgctagtaa ccacaaccct   21912
accatgttca gagcacatgc caggctccat gctgggggctt cgcacgtgtc atcttcacag  21972
tgtccctgtg agtaggtgtg gtttctcttt ccatcttaca aatgagtaaa cagagcctca   22032
gtgtagctaa gtaaccacta ttttaggttt cttagccaat gggtgtgtct gactcctaag   22092
cccatggagg gcattctgag gtggttcaga cagaccccag cttacccttg aacttctgcc   22152
tgctggctgc ataggaggg gctgggggga gtttgagcat ctcaggccat agagccctg    22212
cctcactgtc tccatctctg ggtggaaaga tggtgttttc cctgagaaac taaggctcag   22272
agaggttgaa tggctctccc aaggtcacac agctggtcag ctgcagagtt gagaacacag   22332
gagtcctggt gctcaggcca gcatctcttt ttttctttga gttgtttcta ggtttcctag   22392
ctcttgcctc agaccttaaa gagagagggt ctgatgggga tgggcactgg agacggagca   22452
tcccagcatt tcacatctga gctggctttc ctctgcccca ggc tgc agc tcc cac     22507
                                              Gly Cys Ser Ser His
                                                              565 tgg gag gtg gag gac ctt ggc acc cac aag ccg cct gtg ctg agg cca      22555
Trp Glu Val Glu Asp Leu Gly Thr His Lys Pro Pro Val Leu Arg Pro
            570                 575                 580
```

| | |
|---|---|
| cga ggt cag ccc aac cag tgc gtg ggc cac agg gag gcc agc atc cac<br>Arg Gly Gln Pro Asn Gln Cys Val Gly His Arg Glu Ala Ser Ile His<br>585 590 595 | 22603 |
| gct tcc tgc tgc cat gcc cca ggt ctg gaa tgc aaa gtc aag gag cat<br>Ala Ser Cys Cys His Ala Pro Gly Leu Glu Cys Lys Val Lys Glu His<br>600 605 610 | 22651 |
| gga atc ccg gcc cct cag gag cag gtgaagaggc ccgtgaggcc gggtgggtgg<br>Gly Ile Pro Ala Pro Gln Glu Gln<br>615 620 | 22705 |
| ggtgctgcgt gtctctcctg cacagctttt ctgtgtcagt ttgtgccacc accataccgc | 22765 |
| catacatcag ggtggcggtt tgccaggtag atgctgtggg cagcttccgc cattgtgtgg | 22825 |
| acagcatgta tatgtgtctc tgtgtggctg ggtctgtttt tgcttttgtc cagatcagta | 22885 |
| aggtttgcta cctgggtacc ccactccact tggagtagag tgtgcataaa tatgcataa | 22945 |
| agaaatgcaa tatgcatgca tttattgatt gatctatttt tttctgagat ggggtcttgc | 23005 |
| tgtgttgccc aggctggtct caaattcctg ggctcaagca atcctctggt ctcagcctcc | 23065 |
| ccaagtgttg ggattatagg catgagccgc tgcacctggc ctctctgatc tatttaacaa | 23125 |
| acctgctggg agggtctcag ggtcaggagc agcactgggc tctgaggaca cagagctcac | 23185 |
| tcagccgtga cccagagggg gtgcctgagc tgcatgctga aggttgttag catgaccagc | 23245 |
| aaggcaagaa aaggccctgc cgagattagc aaggcatgtg ccaagccctg gaatgtgaca | 23305 |
| gccgggcctt ctagaaacct gagtgtataa ctctccttaa aagccagtag gagctcctta | 23365 |
| aaaggcagcc ctaaggagtc cactcttaaa tgaactcaga gtcagttta aaatgcaagt | 23425 |
| ctgtgttgat tctggtctgg atggtgcatt cctcgagagc aaaagacagt cttggtcttg | 23485 |
| gatccacttg ccctgggtac actgagggct gctaggttcc aggtgctctt cctggcactg | 23545 |
| gggagggata caggcccaag agacatgctg ttctccctcc tggagcatct attttagtgg | 23605 |
| aggaagacag aaaacaaacc attaatatag agtactgaaa agatgcgatg gagaaaacta | 23665 |
| tagcaaggaa gggaatgggg tgggagagag gtcaggagag gtctcgctga caaggtggac | 23725 |
| gaaacaggcc atgaggcaga gaacatgttc caggcaaagc aaaggccccc aggtgggat | 23785 |
| gtgcagggag taccaggaaa ccagagaggt gggaatagtt atgagatggg gggtgcctca | 23845 |
| gaggggacag ggccaagtca ggtgagacct gagggccaca gtcagcagtg agctggggcc | 23905 |
| atgcagggt ctggcctcag aggagtgtgg tctggcctgg atctgaacct ctcactgtgg | 23965 |
| cctagctgct gagctgagaa gagatgacaa ggaccttggg cagaagcagg gagactggag | 24025 |
| ggaggcggtg gagggtccag gcgttgggc ggggctcagc ctggagtctg aagggagcct | 24085 |
| gcaggcctgg tgggtggatg tgggtgggag aggggagga tggcaccaag gctcgggccc | 24145 |
| ctggacagat ggagttgcca ttaagtggga tgggcaggc tatggggcca tcagtttcag | 24205 |
| agggatgagt ttggcactgg catggtaggc atctgtctat ctccacggcc ctcaaaccag | 24265 |
| gcatgaagca ggagctcacg tgtttggtca gccatggtgc agaaccgcct gggtgggagg | 24325 |
| tgcggggtgg gagatacacg gttgtgtccc aaatgggctc tgagccagcg agggccgtct | 24385 |
| gcactttggc ctcacagaag gatgtcggag ggagaaatga agtgtgggtg ggggtcccgg | 24445 |
| gccacgctag acatgtgctt tcttttcctc gggctctggc ag gtg acc gtg gcc<br>Val Thr Val Ala<br>625 | 24499 |
| tgc gag gag ggc tgg acc ctg act ggc tgc agt gcc ctc cct ggg acc<br>Cys Glu Glu Gly Trp Thr Leu Thr Gly Cys Ser Ala Leu Pro Gly Thr<br>630 635 640 | 24547 |
| tcc cac gtc ctg ggg gcc tac gcc gta gac aac acg tgt gta gtc agg | 24595 |

| | | | | | | | | | | | | |
|---|---|---|---|---|---|---|---|---|---|---|---|---|
| Ser | His | Val | Leu | Gly | Ala | Tyr | Ala | Val | Asp | Asn | Thr | Cys | Val | Val | Arg |
| | | | 645 | | | | 650 | | | | 655 | |

```
agc cgg gac gtc agc act aca ggc agc acc agc gaa gag gcc gtg aca      24643
Ser Arg Asp Val Ser Thr Thr Gly Ser Thr Ser Glu Glu Ala Val Thr
        660                 665                 670 gcc gtt gcc atc tgc tgc cgg agc cgg cac ctg gcg cag gcc tcc cag      24691
Ala Val Ala Ile Cys Cys Arg Ser Arg His Leu Ala Gln Ala Ser Gln
    675                 680                 685 gag ctc cag tga cagccccatc ccaggatggg tgtctgggga gggtcaaggg          24743
Glu Leu Gln
690 ctggggctga gctttaaaat ggttccgact tgtccctctc tcagccctcc atggcctggc    24803 acgaggggat ggggatgctt ccgcctttcc ggggctgctg gcctggccct tgagtgggc     24863 agcctccttg cctggaactc actcactctg ggtgcctcct ccccaggtgg aggtgccagg    24923 aagctccctc cctcactgtg gggcatttca ccattcaaac aggtcgagct gtgctcgggt    24983 gctgccagct gctcccaatg tgccgatgtc cgtgggcaga atgactttta ttgagctctt    25043 gttccgtgcc aggcattcaa tcctcaggtc tccaccaagg aggcaggatt cttcccatgg    25103 ataggggagg gggcggtagg ggctgcaggg acaaacatcg ttgggggtg agtgtgaaag     25163 gtgctgatgg ccctcatctc cagctaactg tggagaagcc cctggggct ccctgattaa     25223 tggaggctta gctttctgga tggcatctag ccagaggctg gagacaggtg tgccctggt     25283 ggtcacaggc tgtgccttgg tttcctgagc cacctttact ctgctctatg ccaggctgtg    25343 ctagcaacac ccaaaggtgg cctgcgggga gccatcacct aggactgact cggcagtgtg    25403 cagtggtgca tgcactgtct cagccaaccc gctccactac ccggcagggt acacattcgc    25463 acccctactt cacagaggaa gaaacctgga accagagggg gcgtgcctgc caagctcaca    25523 cagcaggaac tgagccagaa acgcagattg ggctggctct gaagccaagc ctcttcttac    25583 ttcacccggc tgggctcctc atttttacgg gtaacagtga ggctgggaag gggaacacag    25643 accaggaagc tcggtgagtg atggcagaac gatgcctgca ggcatggaac tttttccgtt    25703 atcacccagg cctgattcac tggcctggcg gagatgcttc taaggcatgg tcgggggaga    25763 gggccaacaa ctgtccctcc ttgagcacca gccccaccca agcaagcaga catttatctt    25823 ttgggtctgt cctctctgtt gccttttac agccaacttt tctagacctg ttttgctttt     25883 gtaacttgaa gatatttatt ctgggttttg tagcatttt attaatatgg tgactttta     25943 aaataaaaac aaacaaacgt tgtcctaact cttgcataga cttgactgcc tagggtgatg    26003 ccttgcttat actaggaact gggtaagttt gttgaatagt tgagtaagcc aagtatttga    26063 tgagtacttg tatcttgagt acaagtattg ggcaagtact ggtgatgtga acttactcct    26123 tgtgcctatc ctaggaatga aatgaatgtc ttcctgcagc tcccctgacc accctgacag    26183 tcaaagtgcc tcctccttgg tgacaggtgc cctacag                             26220
```